United States Patent [19]
Abraham et al.

[11] Patent Number: 5,599,974
[45] Date of Patent: Feb. 4, 1997

[54] ALDEHYDIC AGENTS FOR ALLOSTERIC MODIFICATION OF HEMOGLOBIN

[75] Inventors: Donald J. Abraham, Midlothian; Telih Boyiri, Richmond; Martin Safo, Richmond; Richmond Danso-Danquah, Richmond, all of Va.

[73] Assignee: Center for Innovative Technology, Herndon, Va.

[21] Appl. No.: 308,805

[22] Filed: Sep. 19, 1994

[51] Int. Cl.$^6$ .................................................... C07C 51/42
[52] U.S. Cl. .............................. 562/463; 560/85; 560/86; 560/130; 560/143
[58] Field of Search ............................. 562/463; 560/85, 560/86, 130, 143; 514/544, 568

[56] References Cited

PUBLICATIONS

CA 111:97589 (1989).
CA 118: 82355 (1992).
CA 116: 54888 (1991).
CA 119: 27840 (1993).

Primary Examiner—Paul J. Killos
Attorney, Agent, or Firm—Whitham, Curtis, Whitham & McGinn

[57] ABSTRACT

Chemical compounds which interact inside the central water cavity of hemoglobin and bridge between the two $\alpha$ subunits can be used to allosterically modify hemoglobin towards tense and relaxed states. The functional groups employed are aldehydes and carboxylic acids, wherein the aldehydes form covalent bonds (schiff base) with amino acid residues of hemoglobin and the carboxylic acids form ionic bonds with amino acid residues of hemoglobin. Particularly useful compounds within the practice of this invention bond to the n-terminal valine of one $\alpha$ subunit of hemoglobin, and the lysine 99 and/or arginine 141 of the other $\alpha$ subunit.

28 Claims, 15 Drawing Sheets

α 1-Subunit

α 2-Subunit $NH_3^+$-$Val_1$ $NH_3^+$-$Val_1$

ALDEHYDIC AGENTS FOR ALLOSTERIC MODIFICATION OF HEMOGLOBIN

BACKGROUND OF THE INVENTION

1. Field of the Invention

The invention is generally related to the use of aryl compounds with one or more aldehydic moieties and one or more carboxylic acid moieties to allosterically modify hemoglobin. More particularly, the invention is directed to a method of allosterically modifying hemoglobin with aryl compounds having multiple functional groups, such as aldehydes and carboxylic acids, to stereospecifically cross-link α subunits of the hemoglobin molecule.

2. Description of the Prior Art

Hemoglobin is a tetrameric protein which delivers oxygen via an allosteric mechanism. Oxygen binds to the four hemes of the hemoglobin molecule. Each heme contains porphyrin and iron in the ferrous state. The ferrous ion-oxygen bond is readily reversible. Binding of the first oxygen to a heme requires much greater energy than the second oxygen molecule, binding the third oxygen molecule requires even less energy, and the fourth oxygen requires the lowest energy for binding. Hemoglobin has two α and two β subunits arranged in two fold symmetry. The α and β dimers rotate during oxygen release to open a large central water cavity. It is generally understood that the allosteric transition that involves the movement of the alpha-beta dimer takes place between the binding of the third and fourth oxygen, and the $\alpha_1\beta_1$ interface binding is tighter than the $\alpha_1\alpha_2$ or $\alpha_1\beta_2$ interfaces.

The chemical and physical structure of hemoglobin has been well characterized in the art. Several references, including (Bunn et al., *Human Hemoglobins*, W. B. Saunders Company, London, 1977, and Fermi et al., *Atlas of Molecular Structures in Biology*, ed. Phillips, D.C., Vol. 2, Clarendon Press, Oxford, 1981, which are both herein incorporated by reference) set forth the amino acid sequences of the hemoglobin molecule.

In blood, hemoglobin is in equilibrium between two allosteric structures. In the "T" (for tense) state, hemoglobin is de-oxygenated. In the "R" (for relaxed) state, hemoglobin is oxygenated. An oxygen equilibrium curve can be scanned using well known equipment such as the the Aminco™ Hem-o-scan to evaluate the affinity and degree of cooperativity (allosteric action) of hemoglobin. In the scan, the Y-axis plots the percent of hemoglobin oxygenation and the X-axis plots the partial pressure of oxygen in millimeters of mercury (mm Hg). If a horizontal line is drawn from the 50% oxygen saturation point to the scanned curve and a vertical line is drawn from the intersection point of the horizontal line with the curve to the partial pressure X-axis, a value commonly known as the $P_{50}$ is determined. This is the pressure when the hemoglobin is 50% saturated with oxygen. By comparing the $P_{50}$ value for treated hemoglobin to the $P_{50}$ value for untreated normal adult human hemoglobin (HbA) under physiological conditions (i.e., 37° C., pH=7.4, and partial carbon dioxide pressure of 40 mm Hg), the degree of allosteric modification can be determined. When the $P_{50}$ value for treated hemoglobin is lower than for HbA, a high oxygen affinity hemoglobin is indicated and the curve is said to be "left-shifted". Conversely, when the $P_{50}$ value for treated hemoglobin is higher than for HbA, a low oxygen affinity hemoglobin is indicated and the curve is said to be "right-shifted".

Influencing the allosteric equilibrium of hemoglobin is a viable avenue of attack for treating a wide variety of diseases. For example, several new compounds and methods for treating sickle cell anemia which involve the allosteric regulation of hemoglobin are reported in U.S. Pat. Nos. 4,699,926 to Abraham et al., 4,731,381 to Abraham et al., 4,731,473 to Abraham et al., 4,751,244 to Abraham et al., 4,887,995 to Abraham et al. In addition, new classes of allosteric hemoglobin modifiers described in U.S. Pat. Nos. 5,290,803 to Abraham et al., 5,122,539 to Abraham et al., 5,049,695 to Abraham et al., and 5,248,785 to Abraham et al., have been shown to restore the oxygen carrying capacity of stored blood, and to be useful in treating a variety of disorders such as ischemia, radiotherapy of tumors, respiratory distress syndromes, wound healing, etc.

Aldehydes such as vanillin and 5-(2-formyl-3-hydroxyphenoxy)pentanoic acid have been shown to react with hemoglobin and possess antisickling activity (See, Kreen, G., White, R. D., Br. *J. Pharmacol.*, 1981, 74, 965, and Zaugg, R. H.; Walter, J. A.; Klotz, I. M., *J. Biol. Chem.*, 1977, 252, 8542).

SUMMARY OF THE INVENTION

It is an object of this invention to provide a new class of compounds useful for allosterically modifying hemoglobin.

It is another object of this invention to provide a new class of compounds which interact with hemoglobin at a previously unknown binding site, and which will cross-link the two α subunits of hemoglobin.

It is yet another object of this invention to provide a new method of allosterically modifying hemoglobin.

According to the invention, aryl compounds with aldehydic moieties and carboxylic acid moieties have been found to be useful for allosterically modifying hemoglobin. A particular group of compounds within the scope of this invention stereospecifically cross-link the two α subunits by electrostatic and/or covalent interactions. This group of compounds has been found to bond to a heretofore unknown binding site of hemoglobin.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

In order to develop reagents containing multiple functional groups that will stereospecifically cross-link the two α sub-units of hemoglobin, either by electrostatic (ionic) or covalent (Schiff base) interactions, space filling molecular modeling and other molecular modeling mechanics were performed. A variety of computer aided molecular modeling packages are commercially available. In our investigations, DGEOM, described in Crippen, G. M et al., "Distance Geometry of Molecular Conformation"., Bowden, D., ed. Research Studies Press (Wiley): New York, 1988, HINT, described in Wireko, F. C. et al., *J. Med. Chem.,* 1991, 34, 758, and GRID, described in Goodford, P. J., *J. Med. Chem.,* 1985, 28, 849 were used. All compounds used for the molecular modeling studies were built with either MMOD available from Still et al., (1989) *Macromodel,* (Dept. of Chemistry Columbia University, New York), Version 2.5, or SYBYL, available from Tripos Associates, Inc., St. Louis, Mo., Version 6.03. FRODO available from Evans, P. (1985), Modified FRODO (ed. Res. Cent. Lab. of Mol. Biol., Cambridge, U.K.), version I2.0. and SYBYL run on an EVANS and SUTHERLAND PS390 graphic station. SYBYL was also run on a SILICON graphic station.

FIGS. 1 through 7 present the results of the molecular modeling investigations. Initial molecular modeling studies showed that 5-formylsalicyclic acid (MS1) and 4-carboxybenzaldehyde (MS2) possess the requisite functional groups, orientation, and size to link the α sub-units by a covalent bond to the amino nitrogen of the terminal valine, and also form an electrostatic interaction with the symmetry-related guanidium group of Arg-141. Furthermore, the hydroxyl of MS1 was also determined to form a hydrogen bond with the hydroxyl group of Thr-134. Covalent allosteric modifiers of hemoglobin should advantageously bond with more specificity and higher affinity so as to minimize side reactions with other proteins.

Figure 1:
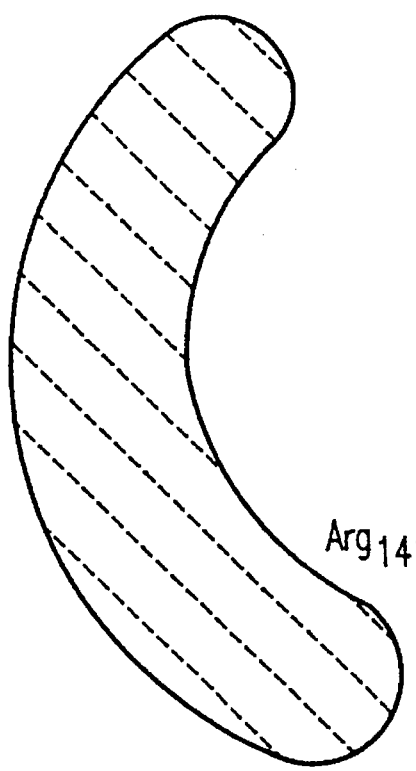
FIG. 1 is a schematic drawing showing the proposed donor site binding area on the $\alpha_1$ and $\alpha_2$ subunits of hemoglobin for a group of molecules of the present invention.
Figure 1:
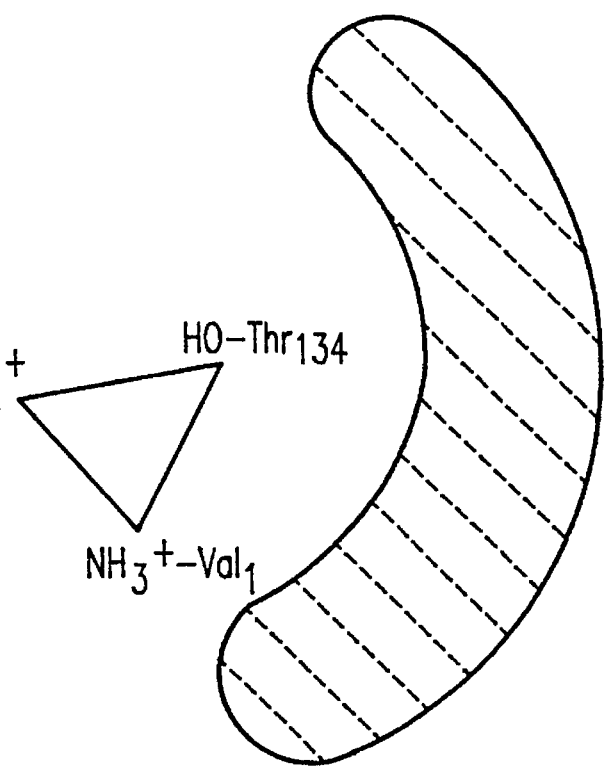
Figure 2:
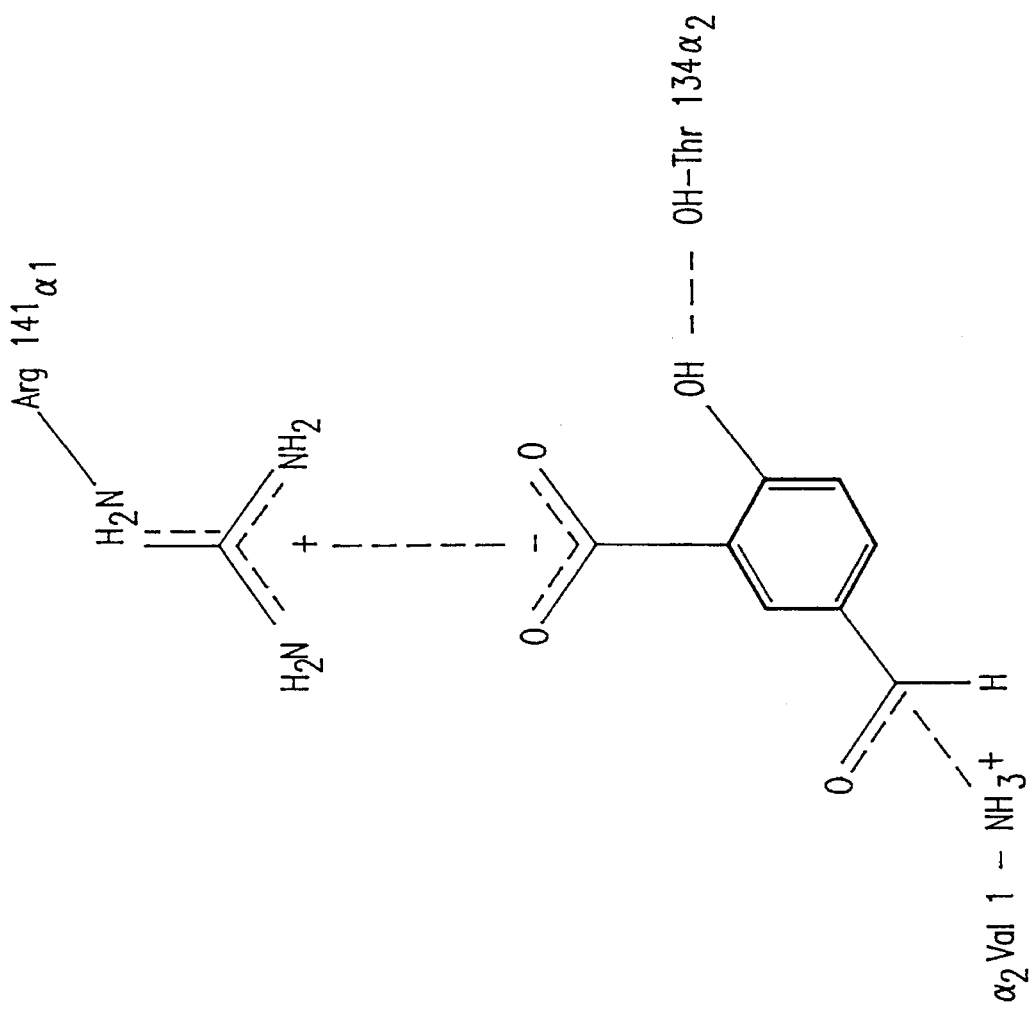
FIG. 2 is a chemical structure diagram of 5-formylsalicyclic acid superimposed on the donor site binding area shown in FIG. 1.
Figure 3:
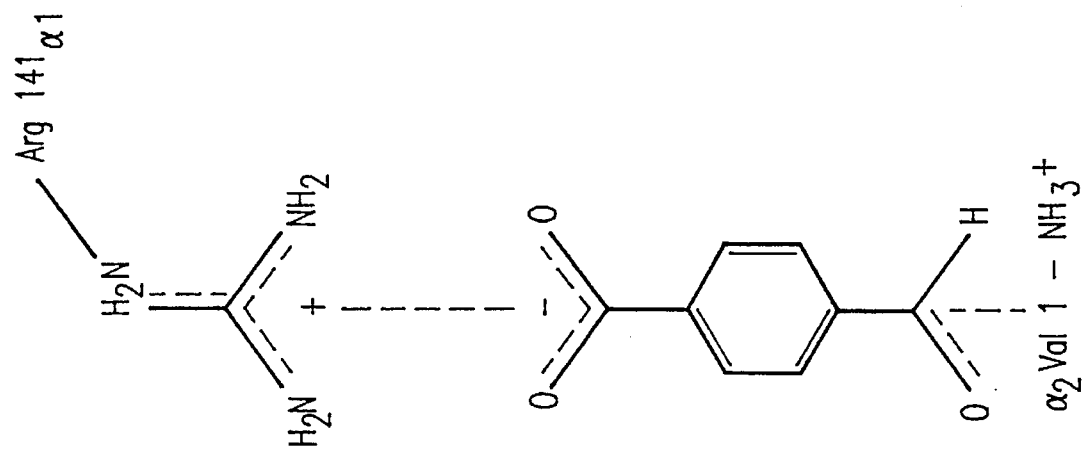
FIG. 3 is a chemical structure diagram of 4-carboxybenzaldehyde superimposed on the donor site binding area shown in FIG. 1.

FIG. 1 shows the proposed binding site of MS1 and MS2 compounds with respect to the $\alpha_1$ and $\alpha_2$ sub-units of hemoglobin. FIGS. 2 and 3 respectively show the superposition of the MS1 and MS2 compounds at the binding site shown in FIG. 1.

Figure 4:
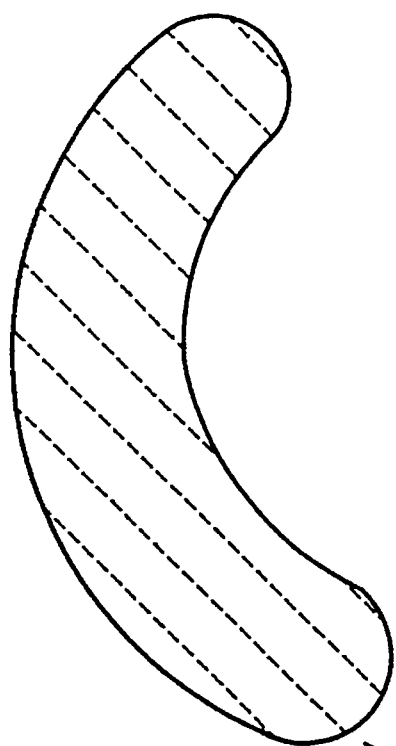
FIG. 4 is a schematic drawing showing a proposed donor site binding area on the $\alpha_1$ and $\alpha_2$ subunits of hemoglobin for dialdehyde molecules of the present invention.
Figure 4:
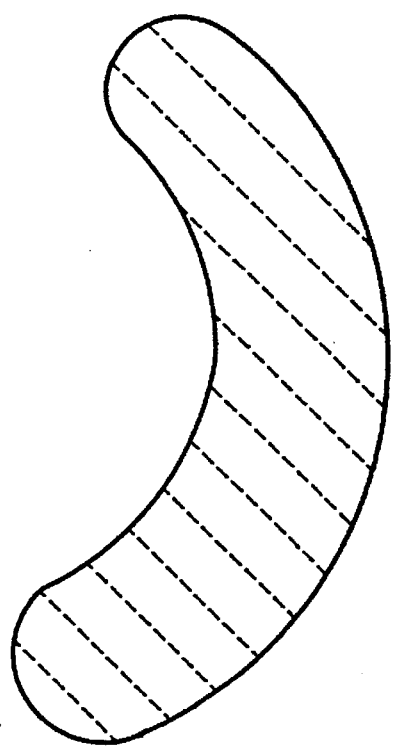
Figure 5:
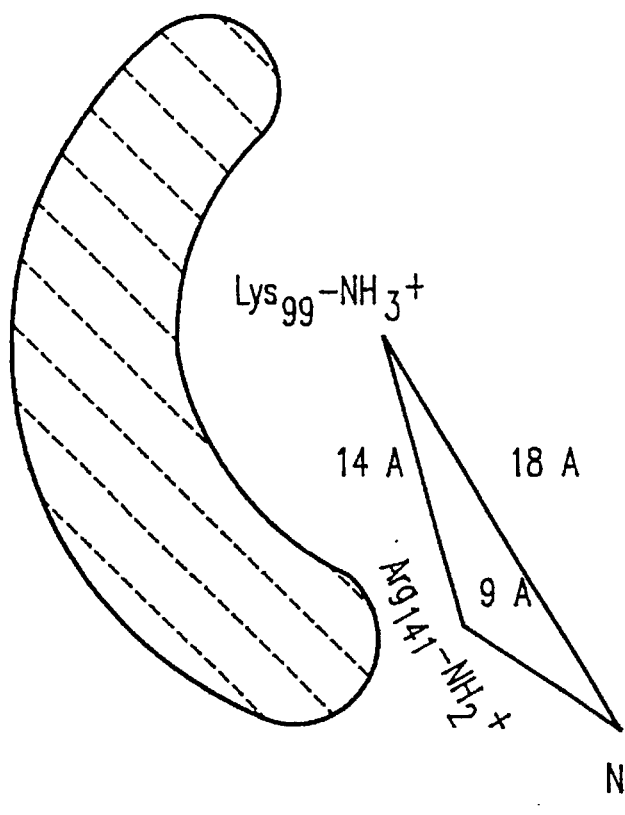
FIG. 5 is a schematic drawing showing another proposed donor site binding area on the $\alpha_1$ and $\alpha_2$ subunits of hemoglobin different from FIG. 4 for dialdehyde molecules of the present invention, wherein the binding site shown in FIG. 5 is a newly discovered binding site in hemoglobin.
Figure 5:
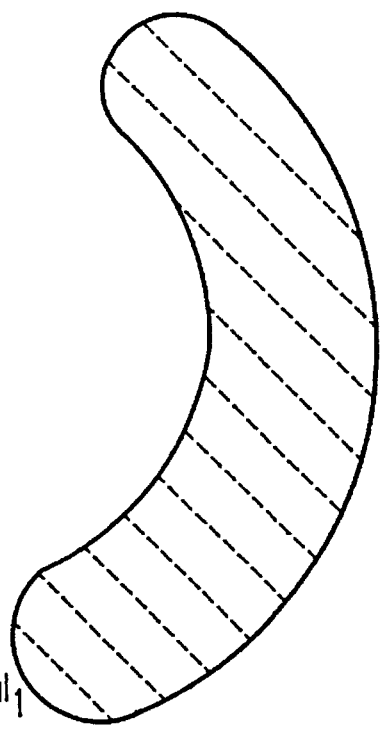
Figure 6:
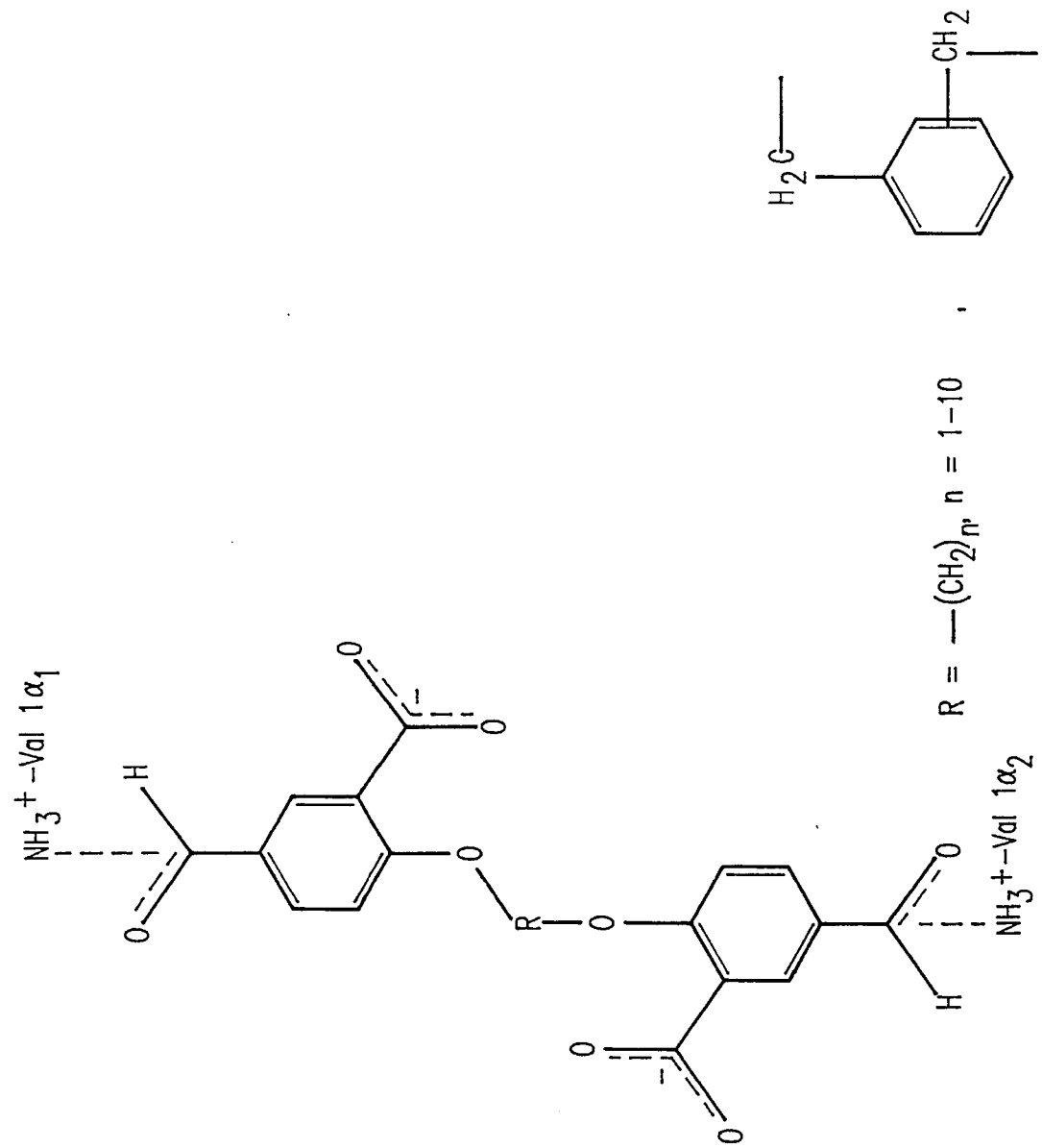
FIG. 6 is a chemical structure diagram of a representative dialdehyde of the present invention superimposed at the Val—Val donor site shown in FIG. 4.
Figure 7:
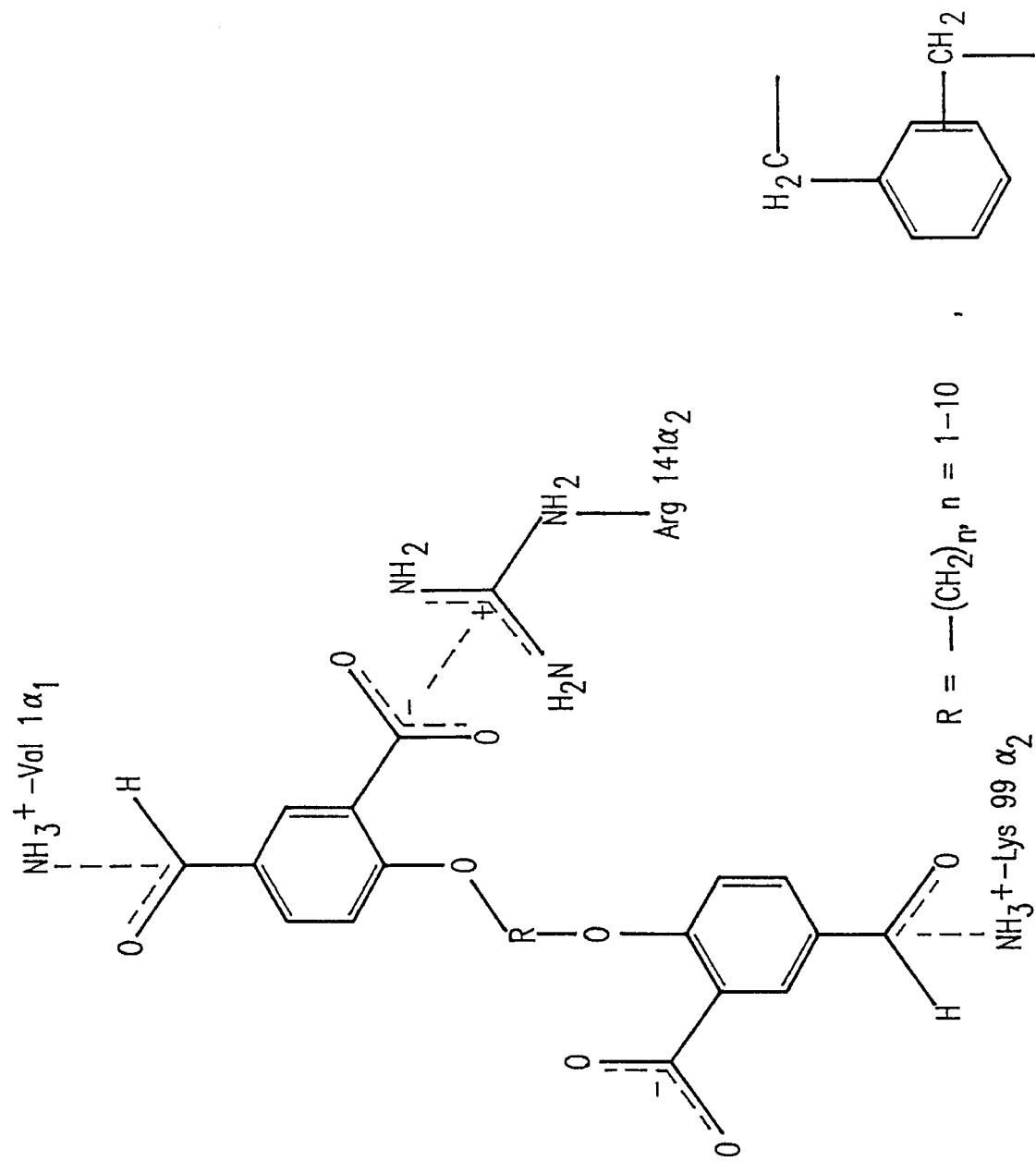
FIG. 7 is a chemical structure diagram of another representative dialdehyde of the present invention superimposed at the Val—Lys donor site shown in FIG. 5.

Additional molecular modeling studies have shown that dialdehyde reagents obtained by linking two molecules of 5-formylsalicyclic acid (MS1) to various aliphatic and aromatic spacers will cross-link the α -subunits by two covalent bonds. This cross-linking may occur between the two terminal amino groups of the symmetry related valines as shown in FIG. 4, or may occur between the symmetry related amino group of the terminal valine and the ϵ-amino group of Lys-99 as shown in FIG. 5. The Val—Lys site shown in FIG. 5 is a completely new binding site in hemoglobin. FIG. 6 shows a representative dialdehyde superimposed at the Val—Val donor site shown in FIG. 4, while FIG. 7 shows a representative dialdehyde superimposed at the Val—Lys donor site shown in FIG. 5.

Compounds which will interact inside the water cavity of hemoglobin and bridge the two α sub-units of hemoglobin can be used to allosterically modify hemoglobin and will be useful in blood substitute preparations, as preparations for augmenting the oxygen carrying capacity of the blood supply, and in the restoration of the oxygen carrying capacity of whole blood. In addition, allosterically modifying hemoglobin is a useful means for treating a wide variety of disorders. For example, left shifters may be useful in the treatment of sickle cell anemia, and right shifters may be useful in treating ischemia, respiratory distress syndroms, cancer, and wound healing, as well as a variety of other disorders, and in inhibiting platelet aggregation, in the radiotherapy of tumors, etc. The compounds may be mixed with blood prior to administration to a human or animal, or be administered directly to a human or animal, or be formulated as a blood substitute.

To test the results deduced from the molecular modeling studies a variety of chemical compounds were synthesized and evaluated. During synthesis, commercial reagents availabe from Aldrich Chemical Co. and Fluka were used. Pure human hemoglobin (HbA) prepared from human blood was supplied by the Army Research Institute, San Diego, Calif. The synthesized products were characterized by $^1$H and $^{13}$C NMR on a GE 300 MHz spectrometer. The spectra are reported in parts per million (δ) downfield with tetramethylsilane as the internal standard. Elemental analysis was conducted at Atlantic Microlab, Inc. in Narcross, Ga. Melting points were determined from a Thomas-Hoover capillary melting point apparatus.

In the oxygen equilibrium studies, the HbA was further purified by dialysis against pH 8.6. Tris buffer (50 mM, containing 40 mg EDTA/L) to remove any residual A2 hemoglobin. The pure HbA fraction was concentrated by using a Schleicher and Schuell colloidion bag apparatus, available from Schleicher and Schuell, Inc., with HEPES buffer (50 mM, pH 7.4) as the exchange buffer. The Hb concentration was determined by using the cyanmet method. The Hb concentration at this point was usually found to be around 35 g% (approximately 5.4 mM). Less than 5% methemoglobin was noted even after several days at 4° C. Oxygen dissociation curves were recorded on an AMINCO Hem-0-Scan oxygen dissociation analyzer available from Travenol Laboratories.

All compounds were dissolved in 50 mM HEPES buffer, pH 7.4, to give 20 mM of drug solution. The Hb (5.4 mM, in HEPES, pH 7.4) and the test compounds (20 mM) were mixed in 1:1 volume ratio (50μL of Hb+50μL of compound solution) to give final concentrations of 2.7 mM and 10mM, respectively (a molar ratio of test compound to hemoglobin of approximately 4:1). A control experiment was prepared by the addition of 50 μL of Hb to 50 μL of HEPES buffer. The mixtures were incubated at 4° C. for two hours before running the oxygen dissociation curves.

In regard to whole-blood studies, the effect of compounds TB17, TB18, and TB19, all of which are described below, on the oxygen affinity of whole blood was determined by mixing 50 μL of freshly drawn heparinized whole blood and 50 μL of test compound (isosmotic and isotonic 50 mM HEPES buffer, pH 7.4, containing 140 mM NaCl, 10 mM glucose), the mixture was equilibrated for 1 hour at 37° C. before analysis.

Reaction of the drug compounds with HbA, crystallization and X-ray data collection of the HbA/drug complexes were performed according to the procedures of Wireko et al., *Proc. Natl. Acad. Sci. USA*, 1991, 88, 2209, which is herein incorporated by reference, with some slight modifications. Freshly prepared solutions of the synthesized compounds in potassium phosphate buffer were incubated at oxy HbA tetramer/drug molar ratios of 1:5 or 1:10 for at least 24 hours. Sodium cyanoborohydrie in phosphate buffer was added in 10- to 50-fold molar excess of HbA tetramer to reduce the Schiff's base adduct for at least 24 hours. The deoxygenated HbA/compound complexes were set up for crystallizations following the procedures described in Perutz et al., *Crys. Growth*, 1968, 2, 54, which is herein incorporated by reference, with some slight modifications. X-ray quality crystals for all complexes were obtained after three to seven days. Crystals of TB19 (discussed below) grown with HbA incubated and reduced under deoxygenated conditions was also used for data collection.

X-ray diffraction data for the MS2 complex (discussed below) was collected using a Rigaku AFC5R rotating anode diffractometer to a resolution of 4Å. All hk±1 reflections and their Friedel pairs were collected. One crystal, dimensions 0.3 to 1.2 mm was used for collection. Diffraction data for the rest of the complexes were collected with a Rigaku AFC5R rotating anode diffractometer equipped with an R-axis IIC image plate system, all to a resolution of 1.94A. Crystals of linear dimensions 0.2 to 0.5 mm were used. Data reduction, structure solution and calculation of Fourier difference electron-density maps were as described in Wireko et al., *Proc. Natl. Acad. Sci. USA*, 1991, 88, 2209. Crystallographic data for all complexes are summarized in Table 3.

Models of the compounds created with MMOD and minimized with MM2 force field were fitted to the electron-density by using FRODO on an EVANS and SUTHERLAND PS390 graphic station.

The synthesis procedures and characterization data for several compounds prepared according to this invention to fit in the binding sites determined by molecular modeling are described below in Examples 1–26. The results of the oxygen dissociation and X-ray analyses are discussed in Examples 27–28.

EXAMPLE 1

Methyl-5-formyl-2-hydroxybenzoate, shown in FIG. 8 as TB0, is synthesized as follows. 5-formylsalicylic acid (5.0 g, 30 mmol) and concentrated sulfuric acid (4 mL, 71 mmol) in methanol (50 mL) were refluxed for 24 hours. The reaction mixture was cooled and evaporated to dryness under reduced pressure. The residual product was dissolved in ethyl acetate and washed thoroughly with aqueous solution of sodium bicarbonate. The organic layer was dried (MgSO$_4$) and evaporated to dryness to give a pale yellow solid; yield 92%; mp 72°–74° C.; $^1$HNNMR (DMSO-d$_6$)d 8.39 (d, 1H, ArH), 8.0 (dd, 1H, ArH), 7.1 (d, 1H, ArH), 4.02 (s, 3H, CH$_3$); Anal. (C$_9$H$_8$O$_4$) calc. C 60.00, H 4.47, found C 60.05, H 4.46.

EXAMPLE 2

Methyl-2-hydroxy-5-acetalbenzoate, shown in FIG. 8 as TB1, is synthesized as follows. Methyl-5-formyl-2-hydroxybenzoate (4.0 g, 22 mmol), ethylene glycol (12 mL, 88 mmol), para-toluene sulfonic acid monohydrate (12.0 mg), and toluene (100 mL) were charged into a round bottom flask fitted with a Dean Stark apparatus and the mixture heated to reflux for 12 hours. The reaction mixture was cooled, washed with aqueous solution of sodium bicarbonate, the organic layer dried (MgSO$_4$) and evaporated under reduced pressure. Flash chromatography using hexane-ethyl acetate 3:1 mixtures as eluent gave a brown viscous liquid as the product; yield 88%; $^1$HNNMR (DMSO-d$_6$)d 10.65 (s, 1H, ArCH-O), 7.89 ( d, 1H, ArH ), 7.59 ( dd, 1H, ArH ), 7.01 (d, 1H, ArH), 5.7 (s, 1H, OH), 3.92–4.1 (m, 4H, CH$_2$CH$_3$), 3.9 (s, 3H, CH$_3$).

EXAMPLE 3

Figure 8:
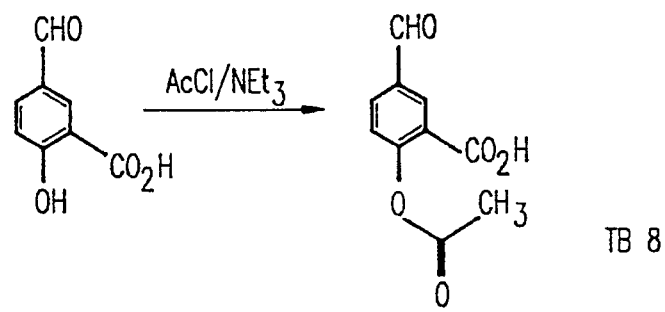
FIG. 8 is a chemical reaction scheme showing the synthesis of a plurality of compounds according to the present invention.
Figure 8:
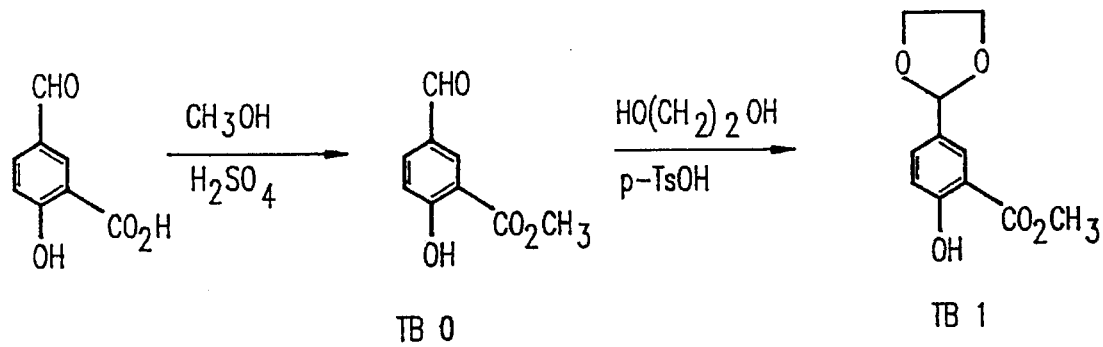
Figure 8:
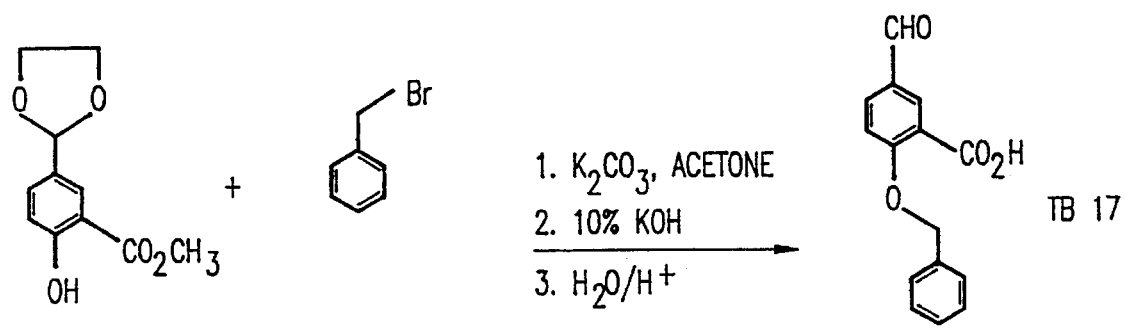
Figure 8:
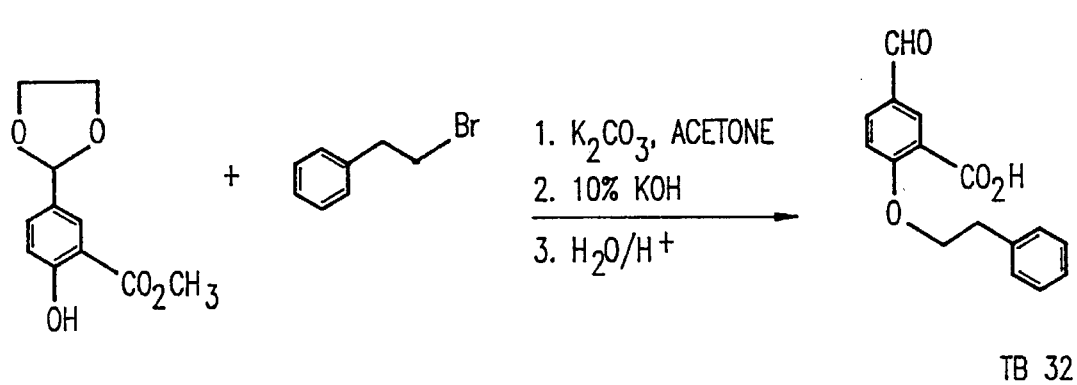

The synthesis of 5-formylaspirin, identified as compound TB8, is shown in FIG. 8. 5-formylsalicylic acid (3.2 g, 20 mmol), acetyl chloride (1.88 g, 20 mmol) and triethylamine (4.08 g, 40 mmol) in 50 mL of dry ether were stirred at room temperature for 5 hours. The reaction mixture was extracted with cold dilute aqueous HCl (0.1 M) and the organic layer washed with cold water. The organic layer was dried over anhydrous MgSO$_4$ and evaporated at reduced pressure. The desired product, 5-formylaspirin crystallized out of ether-petroleum ether solution at 4° C.; yield 70%; mp 115° C.; $^1$H NMR (DMSO-d$_6$) δ 10.02 (s, 1H, CHO), 7.25–8.06 (m, 3H, ArH) , 2.30 (s, 3H, —CH$_3$); Anal. (C$_{10}$H$_8$O$_5$) calc. C 57.69, H 3.87, found C 57.88, H 3.88.

EXAMPLE 4

The synthesis of 2-benzyloxy-5-formylbenzoic acid, identified as compound TB17, is shown in FIG. 8. Methyl-2-hydroxy-5-acetalbenzoate (1.0 g, 4.46 mmol), benzyl bromide (0.76 g, 4.46 mmol) and powdered potassium carbonate (2.0 g, 14.5 mmol) in dry acetone were heated to reflux for 12 hours. The reaction mixture was filtered while hot and the solvent was removed under vacuum. The crude product was flash chromatographed using hexane-ethyl acetate mixtures and the desired intermediate, methyl-2-benzyloxy-5-acetal benzoate, was obtained as a colorless solid. Methyl-2-benzyloxy-5-acetalbenzoate in 10% aqueous potassium hydroxide (20 mL) was heated to reflux for 1 hr, the reaction mixture was filtered, cooooled and acidified with concentrated hydrochloric acid. The precipitate was filtered, washed thoroughly with water (40 mL), redissolved in hot aqueous solution of sodium bicarbonate and extracted with diethyl ether (2×20 mL). The aqueous layer was acidified, the product filtered, washed with small amounts of diethyl ether and air dried; yield 88%; mp 105°–107° C.; $^1$H NMR (DMSO-d$_6$) δ 9.91 (s, 1H, CHO), 7.2–8.6 (m, 8H, ArH) , 5.35 (s, 2H, CH$_2$); Anal. (C$_{15}$H$_{12}$O$_4$) calc. C 70.34, H 4.72, found C 70.17, H 4.99.

EXAMPLE 5

The synthesis of 2-phenylethyloxy-5-formylbenzoic acid, identified as compound TB32, is shown in FIG. 8. Methyl-2,hydroxy-5-acetalbenzoate (1.0g, 4.46 mmol), 2-phenyl-ethyl bromide (0.98 g, 5.27 mmol) and powdered potassium carbonate (2.0 g, 14.5 mmol) in dry acetone were heated to reflux for twelve hours. The reaction mixture was filtered while hot and the solvent was removed under vacuum. The crude product was flash chromatographed using hexane-ethyl acetate mixtures and the desired intermediate, methyl-2-phenylethyloxy-5-acetalbenzoate in 10% potassium hydroxide (20 mL) was heated to reflux for 1 hr., the reaction mixture was filtered, cooled and acidified with concentrated hydrochloric acid. The precipitate was filtered, washed thoroughly with water (40 mL), redissolved in hot aqueous solution of sodium bicarbonate and extracted with diethyl ether (2×20 mL). The aqueous layer was acidified, the product filtered, washed with small amounts of diethyl ether and air dried; yield 80%; mp 112°–114° C.; $^1$H NMR (DMSO-d$_6$) δ 13.05 (s, 1H, CO$_2$H ), 9.92 ( s, 1H, CHO ), 8.19 ( d, 1H, ArH ), 8.01 (dd, 1H, ArH), 7.2–7.45 (m, 6H, ArH), 4.35 (t, 2H, CH$_2$) 3.05 (t, 2H, CH$_2$); Anal. (C$_{16}$H$_{12}$O$_4$•0.25 H$_2$O) calc. C 69.94, H 5.32, found C 70.29, H 5.28.

EXAMPLE 6

Figure 9:
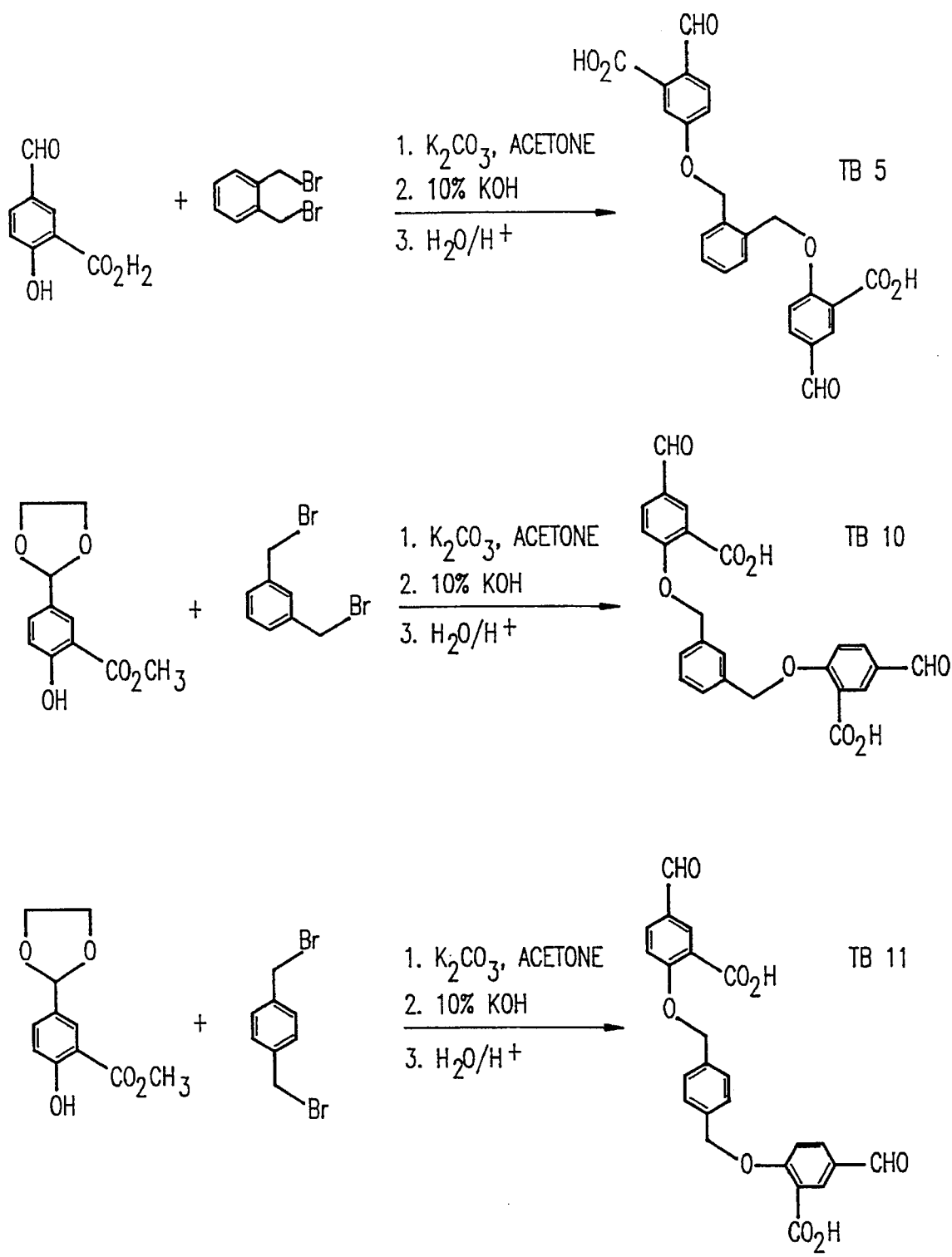
FIG. 9 is a chemical reaction scheme showing the synthesis of additional compounds according to the present invention.

The synthesis of α, α'-bis(2-carboxy-4-formylphenoxy)-o-xylene, identified as compound TB5, is shown in FIG. 9. Methyl-2-hydoxy-5-acetalbenzoate (1.0 g, 4.46 mmol), α,α'-dibromo-o-xylene (0.59 g, 2.23 mmol) and powdered potassium carbonate (2.0 g, 14.5 mmol) in dry acetone were heated to reflux for twelve hours. The reaction mixture was filtered while hot and the solvent was removed under vacuum. The gummy residue was flash chromatographed using hexane-ethyl acetate mixtures to obtain the desired intermediate diester. The diester, in 10% potassium hydroxide (30 mL), was heated to reflux for 1 hour, the reaction mixture was filtered, cooled and acidified with concentrated hydrochloric acid. The precipitate was filtered, washed thoroughly with water (40 ml), redissolved in hot aqueous solution of sodium bicarbonate and extracted with diethyle ether (2×20 mL). The aqueous layer was acidified, the product filtered, washed with small amounts of diethyl ether and air dried; yield 54%; mp 200° C. (dec.); $^1$H NMR (DMSO-d$_6$) δ 13.15 (b, 2H, CO$_2$H), 9.95 (s, 2H, CHO), 7.4–8.25 (m, 10H, ArH), 5.55 (s, 4H, CH$_2$); Anal. (C$_{24}$H$_{12}$O$_4$) calc. C 66.36, H 4.18, found C 66.35, H 4.22.

EXAMPLE 7

The synthesis of α,α'bis(2-carboxy-4-formylphenoxy)-m-xylene, identified as compound TB10, is shown in FIG. 9. Methyl-2-hydroxy-5-acetalbenzoate (1.0 g, 4.46 mmol), α,α'-dibromo-m-xylene (0.59 g, 2.23 mmol) and powdered potassium carbonate (2.0 g, 14.5 mmol) in dry acetone were heated to reflux for 12 hr. The reaction mixture was filtered while hot and the solvent was removed under vacuum. The gummy residue was flash chromatographed using hexane-ethyl acetate mixtures to obtained the desired intermediate diester. The diester in 10% potassium hydroxide (30 mL) was heated to reflux for 1 hr, the reaction mixture was filtered, cooled and acidified with concentrated hydrochloric acid. The precipitate was filtered, washed thoroughly with water (40 mL), redissolved in hot aqueous solution of sodium bicarbonate and extracted with diethyl ether (2×20 mL). The aqueous layer was acidified, the product filtered, washed with small amounts of diethyl ether and air dried; yield 72%; mp 218°–220° C.; $^1$HNMR (DMSO-d$_6$) δ 13.1 (b, 2H, CO$_2$H), 9.95 (s, 2H,CHO), 7.4–8.25 (m, 10H, ArH), 5.35 (s, 4H, CH$_2$); Anal. (C$_{24}$H$_{18}$O$_8$•0.5H$_2$O) calc. C 65.01, H 4.32, found C 65.01, H 4.27.

EXAMPLE 8

The synthesis of α,α'bis(2-carboxy-4-formylphenoxy)-p-xylene, identified as compound TB11, is shown in FIG. 9. Methyl-2-hydroxy-5-acetalbenzoate (1.0 g, 4.46 mmol), α,α'-dibromo-p-xylene (0.59 g, 2.23 mmol) and powdered potassium carbonate (2.0 g, 14.5 mmol) in dry acetone were heated to reflux for 12 hr. The reaction mixture was filtered while hot and the solvent was removed under vacuum. The gummy residue was flash chromatographed using hexane-ethyl acetate mixtures to obtained the desired intermediate diester. The diester in 10% potassium hydroxide (30 mL) was heated to reflux for 1 hr, the reaction mixture was filtered, cooled and acidified with conc. hydrochloric acid. The precipitate was filtered, washed thoroughly with water (40 mL), re-disolved in hot aqueous solution of sodium bicarbonate and washed with diethyl ether (2×20 mL). The aqueous layer was acidified, the product filtered, washed with small amounts of diethyl ether and air dried; yield 96%; mp 220°–222° C.; $^1$HNMR (DMSO-d$_6$) δ 13.05 (b, 2H, CO$_2$H), 9.95 (s, 2H, CHO), 7.42–8.2 (m, 10H, ArH), 5.35 (s, 4H, CH$_2$); Anal. (C$_{24}$H$_{18}$O$_8$•0.75H$_2$O) calc. C 64.36, H 4.36, found C 64.29, H 4.24.

EXAMPLE 9

Figure 10:
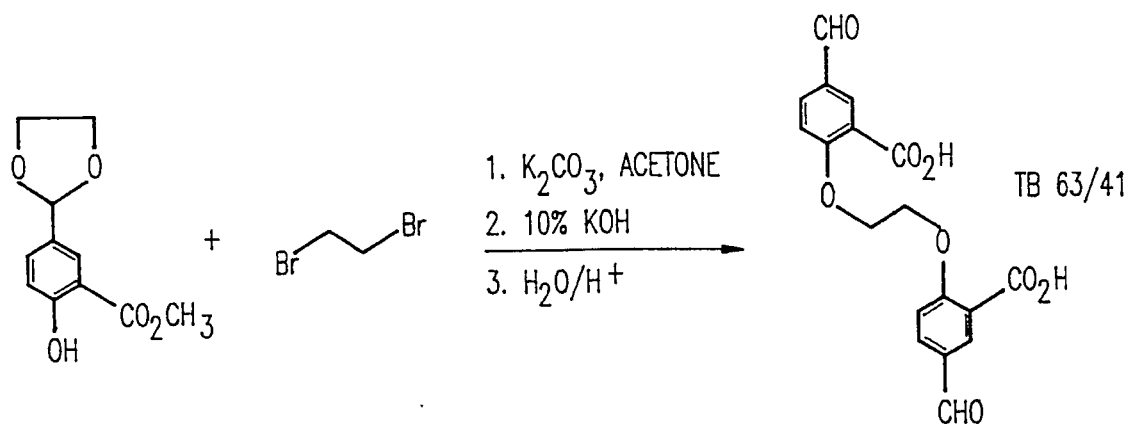
FIG. 10 is a chemical reaction scheme showing the synthesis of additional compounds according to the present invention.
Figure 10:
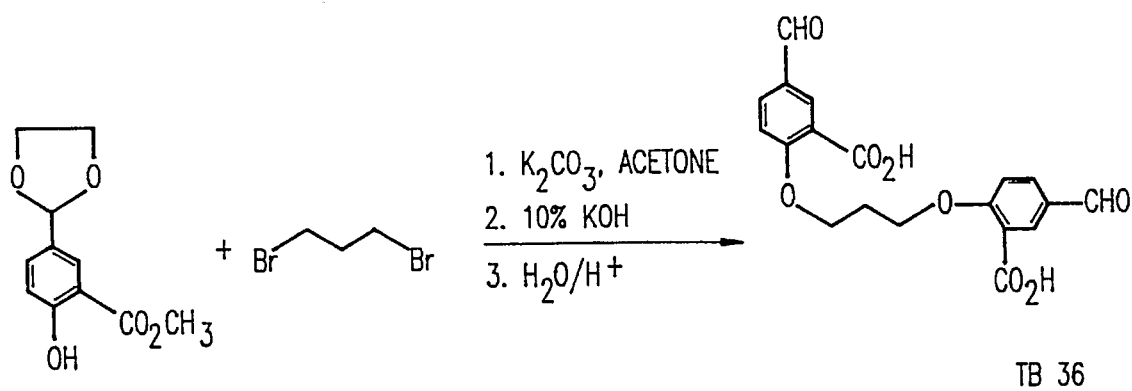
Figure 10:
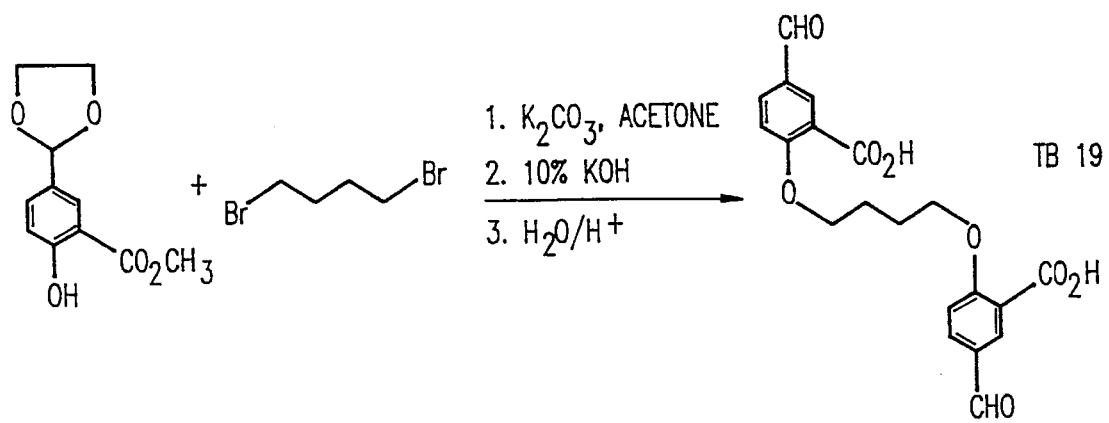

The synthesis of 1,4-Bis(2-carboxy-4-formylphenoxy)-butane, identified as compound TB19, is shown in FIG. 10. Methyl-2-hydroxy-5-acetalbenzoate (1.0 g, 4.46 mmol), 1,4-dibromobutane (0.48 g, 2.23 mmol) and powdered potassium carbonate (2.0 g, 14.5 mmol) in dry acetone were heated to reflux for 12 hr. The reaction mixture was filtered while hot and the solvent was removed under vacuum. The gummy residue was flash chromatographed using hexane-ethyl acetate mixtures to obtained the desired intermediate diester. The diester in 10% potassium hydroxide (30 mL) was heated to reflux for 1 hr, the reaction mixture was filtered, cooled and acidified with conc. hydrochloric acid. The precipitate was filtered, washed thoroughly with water (40 mL), redissolved in hot aqueous solution of sodium bicarbonate and extracted with diethyl ether (2×20 mL ) . The aqueous layer was acidified, the product filtered, washed with small amounts of diethyl ether and air dried; yield 95% mp 215° C. (dec.); $^1$HNMR (DMSO-d$_6$) δ 12.9 (b, 2H, CO$_2$H), 9.89 (s, 2H, CHO), 7.3–8.15 (m, 6H, ArH), 4.2 (b, 4H, CH$_2$O), 1.9 (b, 4H, CH$_2$); Anal.. (C$_{20}$H$_{18}$O$_8$•0.25H$_2$O) calc. C 61.46, H 4.77, found C 61.29, H 4.69.

EXAMPLE 10

Figure 11:
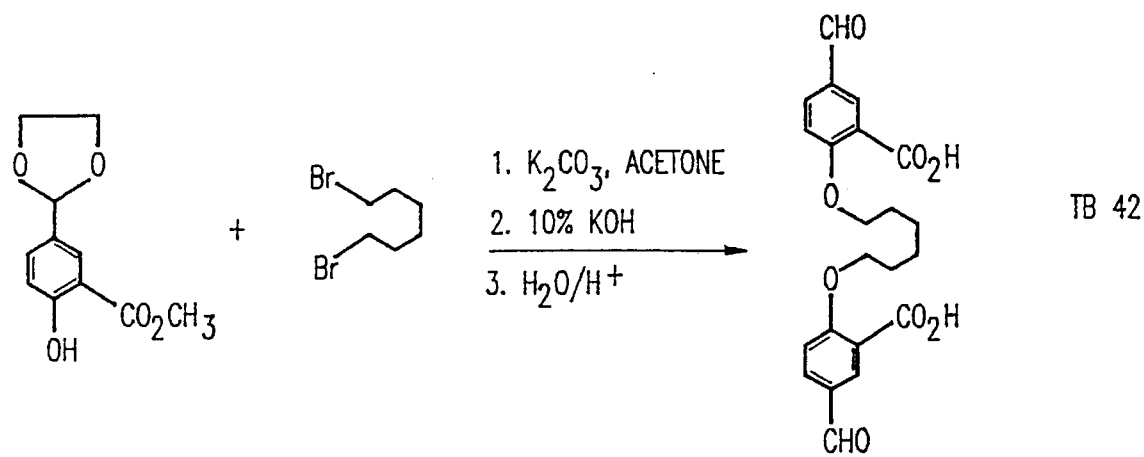
FIG. 11 is a chemical reaction scheme showing the synthesis of additional compounds according to the present invention.
Figure 11:
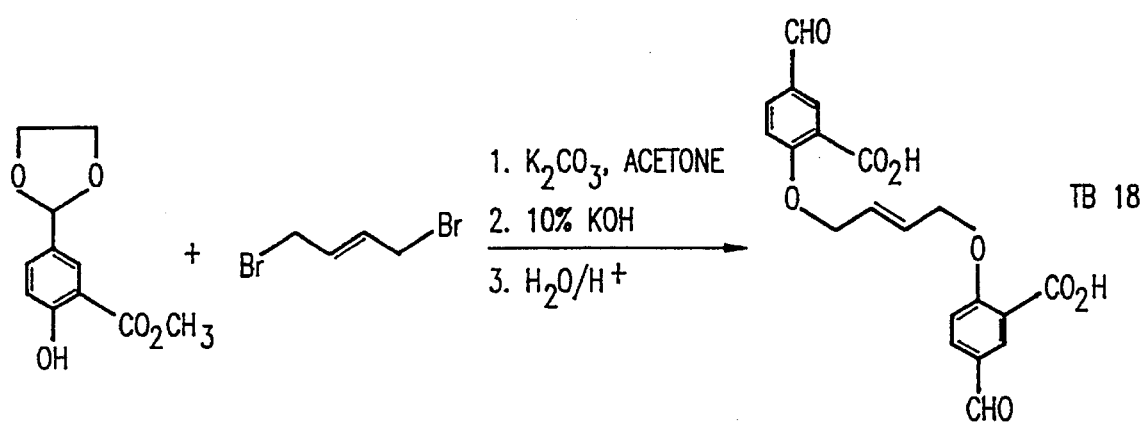
Figure 11:
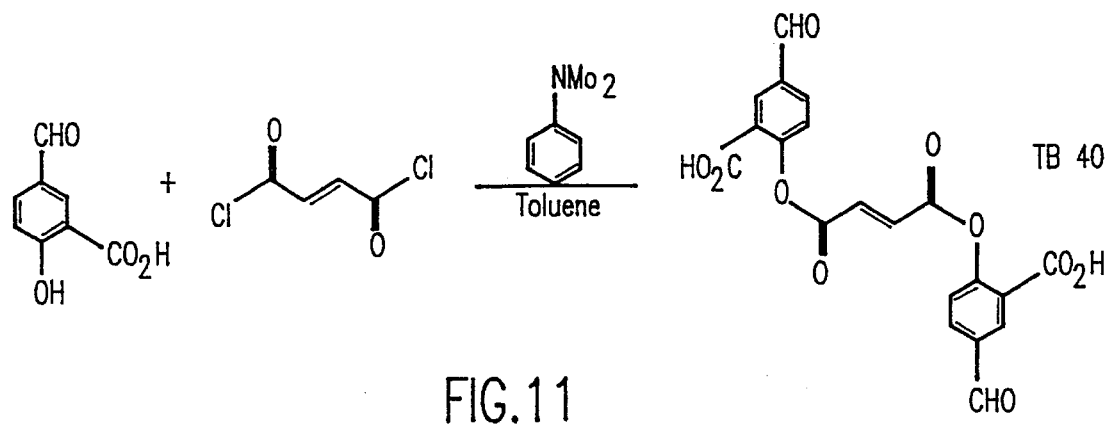

The synthesis of 1,6-bis(2-carboxy-4-formylphenoxy)-hexane, identified as compound TB42, is shown in FIG. 11. Methyl-2-hydroxy-5-acetalbenzoate (1.0 g, 4.46 mmol), 1,6-dibromohexane (0.54 g, 2.23 mmol) and powdered potassium carbonate (2.0 g, 14.5 mmol) in dry acetone were heated to reflux for 12 hr. The reaction mixture was filtered while hot and the solvent was removed under vacuum. The residue was flash chromatographed using hexane-ethyl acetate mixtures to obtained the desired intermediate diester. The diester in 10% potassium hydroxide (30 mL) was heated to reflux for 30 min, the reaction mixture was filtered, cooled and acidified with concentrated hydrochloric acid. The precipitate was filtered, washed thoroughly with water (40 mL), re-dissolved in hot aqueous solution of sodium bicarbonate and extracted with diethyl ether (2×20 mL ) . The aqueous layer was acidified, the product filtered, washed with small amounts of diethyl ether and air dried; yield 70%; mp 149° C. (dec.); $^1$HNMR (DMSO-$d_6$) δ 9.90 (s, 2H, CHO), 8.19 (d, 2H, ArH), 8.02 (dd, 2H, ArH), 7.31 (d, 2H, ArH), 4.18 (t, 4H, $CH_2O$), 1.75 (m, 4H, $CH_2$), 1.51 (m, 4H, $CH_2$) . Anal. ($C_{22}H_{22}O_8$•0.5$H_2O$) calc. C 62.41, H 5.48, found C 62.60, H 5.42.

EXAMPLE 11

The synthesis of 1,2-Bis(2-Carboxy-4-formylphenoxy)-ethane, identified as compound TB41, is shown in FIG. 10. Methyl-2-hydroxy-5-acetalbenzoate (1.0 g, 4.46 mmol), 1,2-dibromoethane (0.42 g, 2.23 mmol) and powdered potassium carbonate (2.0 g, 14.5 mmol) in dry acetone were heated to reflux for 12 hr. The reaction mixture was filtered while hot and the solvent was removed under vacuum. The residue was flash chromatographed using hexane-ethyl acetate mixtures to obtained the desired intermediate diester. The diester in 10% potassium hydroxide (30 mL) was heated to reflux for 1 hr, the reaction mixture was filtered, cooled and acidified with concentrated hydrochloric acid. The precipitate was filtered, washed thoroughly with water (40 mL), re-dissolved in hot aqueous solution of sodium bicarbonate and extracted with diethyl ether (2×20 mL). The aqueous layer was acidified, the product filtered, washed with small amounts of diethyl ether and air dried; yield 75%; mp 191° C.(dec.); $^1$HNMR (DMSO-$d_6$) δ 9.91 (s, 2H, CHO), 8.2 (d, 2H, ArH), 8.06 (dd, 2H, ArH), 7.49 (d,2H, ArH), 4.59 (s, 4H, $CH_2 CH_2$); Anal. ($C^{18}H^{14}O^8$) calc. C 60.33, H 3.95, found C 60.64, H 3.65.

EXAMPLE 12

The synthesis of 1,3-bis(2-carboxy-4-formylphenoxy)-propane, identified as compound TB36, is shown in FIG. 10. Methyl-2-hydroxy-5-acetalbenzoate (1.0 g, 4.46 mmol), 1,3-dibromopropane (0.46 g, 2.23 mmol) and powdered potassium carbonate (2.0 g, 14.5 mmol) in dry acetone were heated to reflux for 12 hr. The reaction mixture was filtered while hot and the solvent was removed under vacuum. The residue was flash chromatographed using hexane-ethyl acetate mixtures to obtained the desired intermediate diester. The diester in 10% potassium hydroxide (30 mL) was heated to reflux for 30 min, the reaction mixture was filtered, cooled and acidified with conc. hydrochloric acid. The precipitate was filtered, washed thoroughly with water (40 mL), redissolved in hot aqueous solution of sodium bicarbonate and extracted with diethyl ether (2×20 mL). The aqueous layer was acidified, the product filtered, washed with small amounts of diethyl ether and air dried; yield 90%; mp 192° C. (dec.); $^1$HNMR (DMSO-$d_6$) & 13.0 (b, 2H, $CO_2H$) , 9.95 (s,2H, CHO), 8.2 (d, 2H, ArH), 8.05 (dd, 2H, ArH), 7.39 (d, 2H, ArH), 4.4 (t, 4H, $CH_2$), 2.25 (t, 2H, $CH_2$); Anal. ($C_{19}H_{16}O_8$) calc. C 61.29, H 4.33, found C 61.62, H 4.66.

EXAMPLE 13

The synthesis of 1,4-bis(2-carboxy-4-formylphenoxy)-2-butene, identified as compound TB18, is shown in FIG. 11. Methyl-2-hydroxy-5-acetalbenzoate (1.0 g, 4.46 mmol), 1,4-dibromo-2-butene (0.48 g, 2.23 mmol) and powdered potassium carbonate (2.0 g, 14.5 mmol) in dry acetone were heated to reflux for 12 hr. The reaction mixture was filtered while hot and the solvent was removed under vacuum. The gummy residue was flash chromatographed using hexane-ethyl acetate mixtures to obtained the desired intermediate diester. The diester in 10% potassium hydroxide (30 mL) was heated to reflux for 1 hr, the reaction mixture was filtered, cooled and acidified with concentrated hydrochloric acid. The precipitate was filtered, washed thoroughly with water (40 mL), redissolved in hot aqueous solution of sodium bicarbonate and extracted with diethyl ether (2×20 mL). The aqueous layer was acidified, the product filtered, washed with small amounts of diethyl ether and air dried; yield 92%; mp 211°–213° C.; $^1$HNMR (DMSO-$d_6$) δ 12.35 (b, 2H, $CO_2H$), 9.95 (2H, s, CHO), 7.35–8.25 (m, 6H, ArH), 6.25 (b, 2H, CH=CH), 4.85 (b, 4H, $CH_2$); Anal. ($C_{20}H_{16}O_9$•0.5$H_2O$) calc. C61.07, H 4.36, found C 61.31, H 4.30.

EXAMPLE 14

The synthesis of bis(2-carboxy-4-formylphenoxy)-fumerate, identified as compound TB40, is shown in FIG. 11. To a solution of fumeryl chloride (1.53 g, 10 mmol) in dry toluene (50 ml) was added 5-formylsalicylic (1.66 g, 10 mmol) and N, N-dimethylaniline ( 2.4 g, 20 mmol) , and the mixture was stirred overnight at 25° C. Water (30 mL) and concentrated hydrchloride acid (5 mL) were added and the mixture was stirred for 20 min. and filtered. The solid product was washed twice with cold water and recrystallized from acetone/hexane to yield the desired product (64% yield); mp 180°–182° C.; $^1$HNMR (DMSO-$d_6$) δ 10.1 (s, 2H, CHO), 8.53 (d, 2H, ArH), 8.23 (dd, 2H, ArH), 7.63 (d, 2H, ArH), 7.28 (s, 2H, CH=CH); Anal. ($C_{20}H_{12}O_{10}$•$H_2O$) calc. C 55.82, H 3.28, found C 55.70, H 3.27.

EXAMPLE 15

Figure 12:
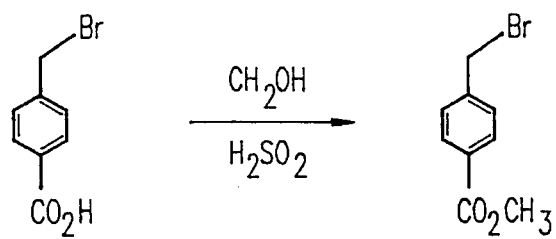
FIG. 12 is a chemical reaction scheme showing the synthesis of additional compounds according to the present invention.
Figure 12:
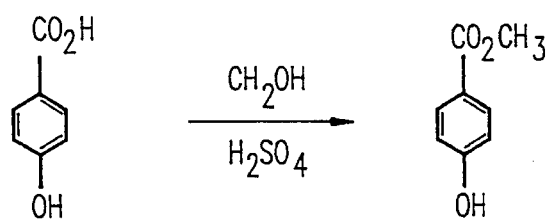
Figure 12:
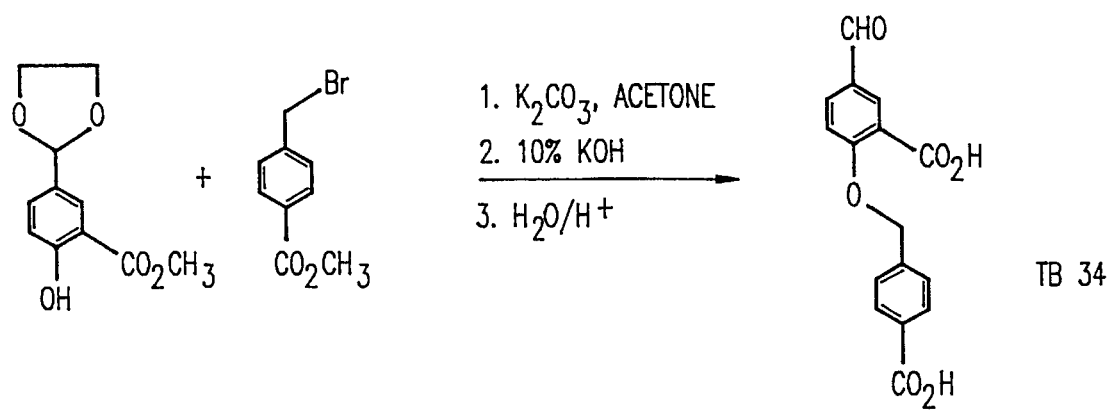
Figure 12:
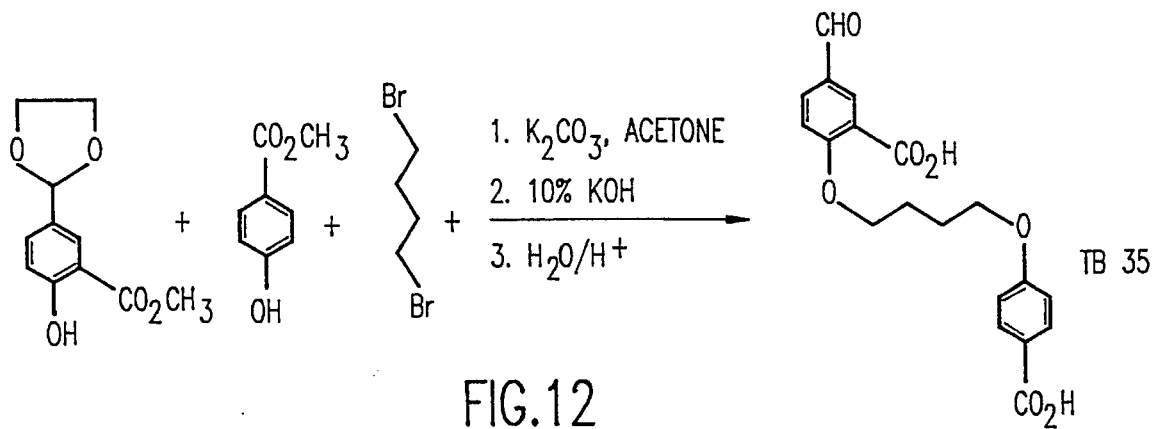

The synthesis of 1-[(2-carboxy-4-formylphenoxy)]-4-[4-carboxyphenoxy)]-butane, identified as compound TB35, is shown in FIG. 12. Methyl-2-hydroxy-5-acetalbenzoate (1.0 g, 4.46 mmol), methyl-4-hydroxybenzoate (0.68 g, 4.46 mmol), 1,4-dibromobutane (0.96 g, 4.46 mmol) and powdered potassium carbonate (4.0 g, 29 mmol) in dry acetone were heated to reflux for 12 hr. The reaction mixture was filtered while hot and the solvent was removed under vacuum. The gummy residue was flash chromatographed using hexane-ethyl acetate mixtures to obtain the desired intermediate diester. The diester in 10% potassium hydroxide (50 mL) was heated to reflux for 1 hr, the reaction mixture was filtered, cooled and acidified with concentrated hydrochloric acid. The precipitate was filtered, washed thoroughly with water (40 mL), redissolved in hot aqueous solution of sodium bicarbonate and extracted with diethyl ether (2×20 mL ) . The aqueous layer was acidified, the product filtered, washed with small amounts of diethyl ether and air dried; yield 82%, mp 185° C. (dec.); $^1$HNMR (DMSO-$d_6$) δ 12.85 (b, 2H, $CO_2H$), 9.9 (s, 2H, CHO), 8.2 (d, 1H, ArH), 8.05 (dd, 1H, ArH), 7.9 (d, 2H, ArH), 7.36 (d, 1H, ArH), 7.01 (d, 2H, ArH) 4.25 (b, 2H, $CH_2O$), 4.11 (b, 2H, $CH_2O$) , 1.95 (b, 4H, $CH_2$); Anal. ($C_{19}H_{18}O_7$•$H_2O$) calc. C 60.64, H 5.36, found C 60.76, H 5.11.

EXAMPLE 16

The synthesis of α-(2-carboxy-4-formylphenoxy)-p-toluic acid, identified as compound TB34, is shown in FIG. 12. Methyl-2-hydroxy-5-acetalbenzoate (1.0 g, 4.46 mmol), 4-(methylcarboxy)benzylbromide (1.02 g, 4.46 mmol) and powdered potassium carbonate (2.0 g, 14.5 mmol) in dry acetone were heated to reflux for 12 hr. The reaction mixture was filtered while hot and the solvent was removed under vacuum. The crude product was flash chromatographed using hexane-ethyl acetate mixtures and the desired intermediate, was obtained as a colorless solid. The intermediate was heated in 10% potassium hydroxide (20 mL) to reflux for 1 hr, the reaction mixture was filtered, cooled and acidified with concentrated hydrochloric acid. The precipitate was filtered, washed thoroughly with water (40 mL), redissolved in hot aqueous solution of sodium bicarbonate and extracted with diethyl ether (2×20 mL). The aqueous layer was acidified, the product filtered, washed with hexane and small amounts of diethyl ether and air dried; yield 90%; mp 215° C.; $^1$HNMR (DMSO-$d_6$) δ 9.91 (s, 1H, CHO), 8.39 (d, 1H, ArH), 7.9–8.06 (m, 3H, ArH), 7.45 (d, 2H, ArH), 7.15 (d, 1H, ArH), 4.5 (s, 2H, $CH_2$); Anal. ($C_{16}H_{12}O_6 \cdot 1.5H_2O$) calc. C 59.54, H 4.53, found C 59.82, H 4.23.

EXAMPLE 17

Figure 13:
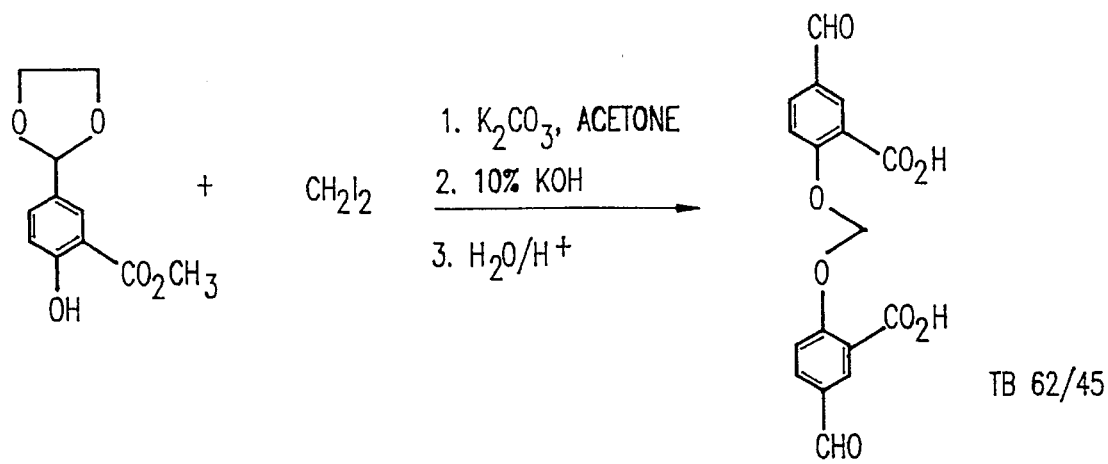
FIG. 13 is a chemical reaction scheme showing the synthesis of additional compounds according to the present invention.
Figure 13:
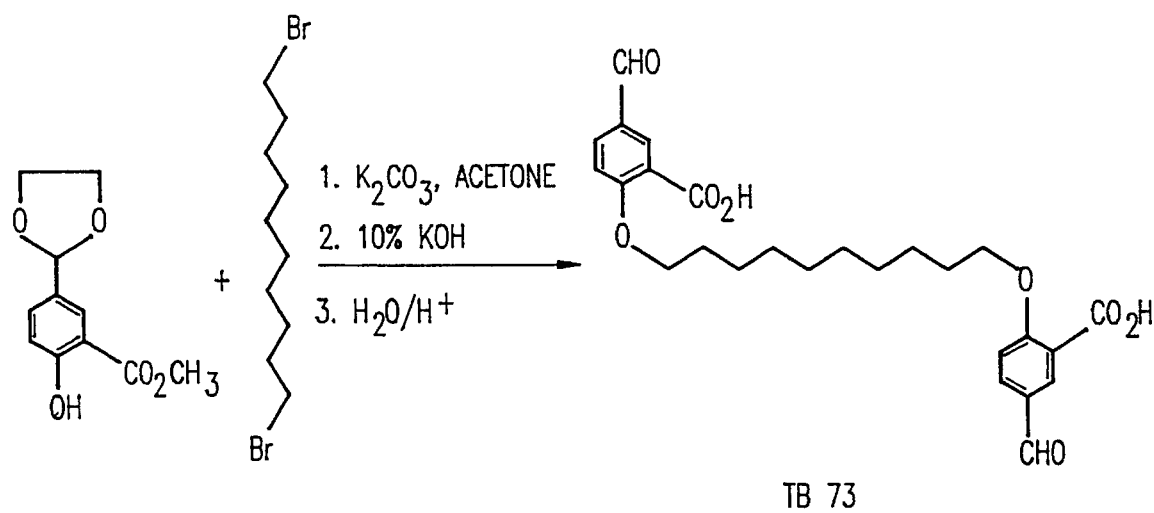

The synthesis of bis(2-carboxy-4-formylphenoxy)-methane, identified as compound TB45, is shown in FIG. 13. Methyl-2-hydroxy-5-acetalbenzoate (1.0 g, 4.46 mmol), diiodomethane (0.6 g, 2.24 mmol) and powdered potassium carbonate (2.0 g, 14.5 mmol) in dry acetone were heated to reflux for 24 hr. The reaction mixture was filtered while hot and the solvent was removed under vacuum. The residue was flash chromatographed using hexane-ethyl acetate mixtures to obtained the desired intermediate diester. The diester in 10% potassium hydroxide (30 mL) was heated to reflux for 1 hr, the reaction mixture was filtered, cooled and acidified with concentrated hydrochloric acid. The precipitate was filtered, washed thoroughly with water (40 mL), redissolved in hot aqueous solution of sodium bicarbonate and extracted with diethyl ether (2×20 ml). The aqueous layer was acidified, the product filtered, washed with small amounts of diethyl ether and air dried; yield 85%; mp 220° C. (dec.); $^1$HNMR (DMSO-$d_6$) δ 9.91 (s, 2H, CHO), 8.2 (d, 2H, ArH), 8.05 (dd, 2H, ArH), 7.55 (d, 2H, ArH), 6.18 (s, 2H, ArOCH$_2$OAr); Anal. ($C_{17}H_{12}O_8$) calc. C 59.30, H 3.3.52, found C 59.52, H 3.5.

EXAMPLE 18

Figure 14:
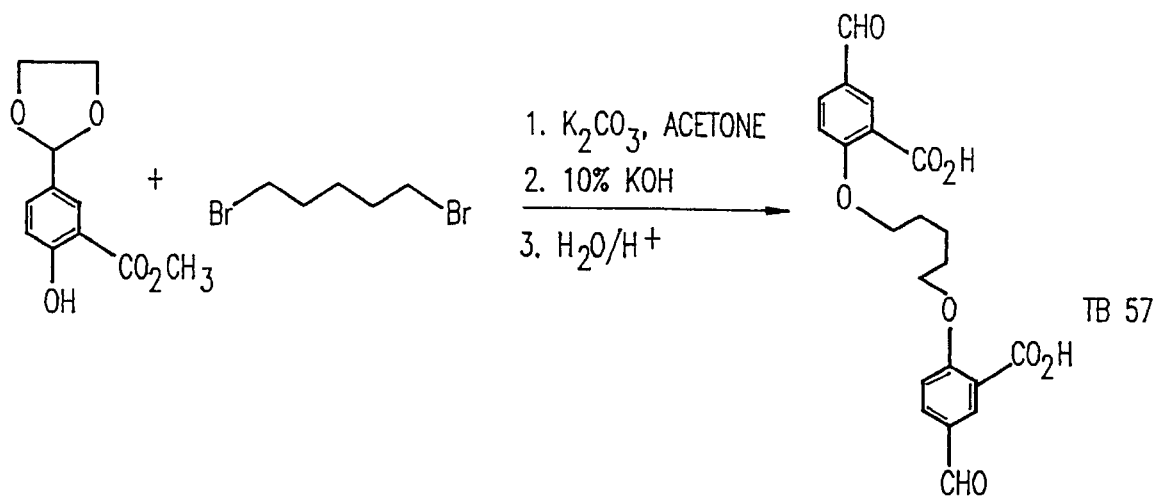
FIG. 14 is a chemical reaction scheme showing the synthesis of additional compounds according to the present invention.
Figure 14:
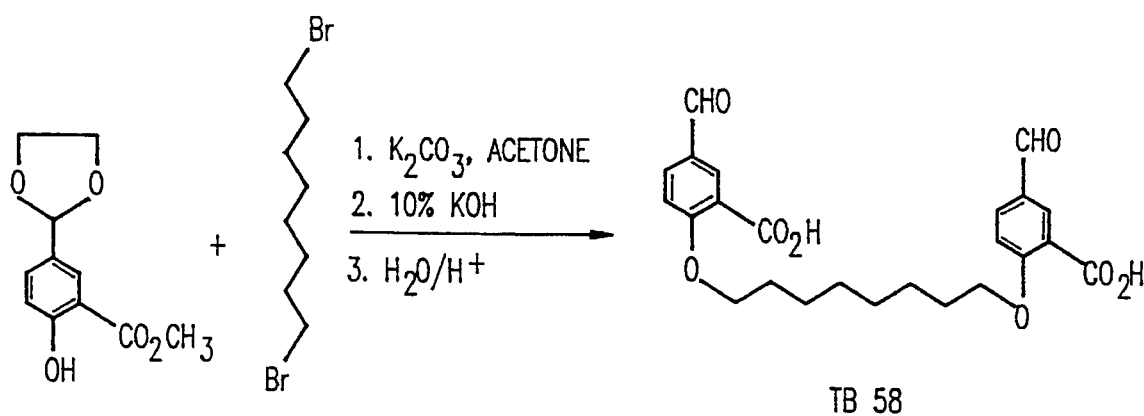
Figure 14:
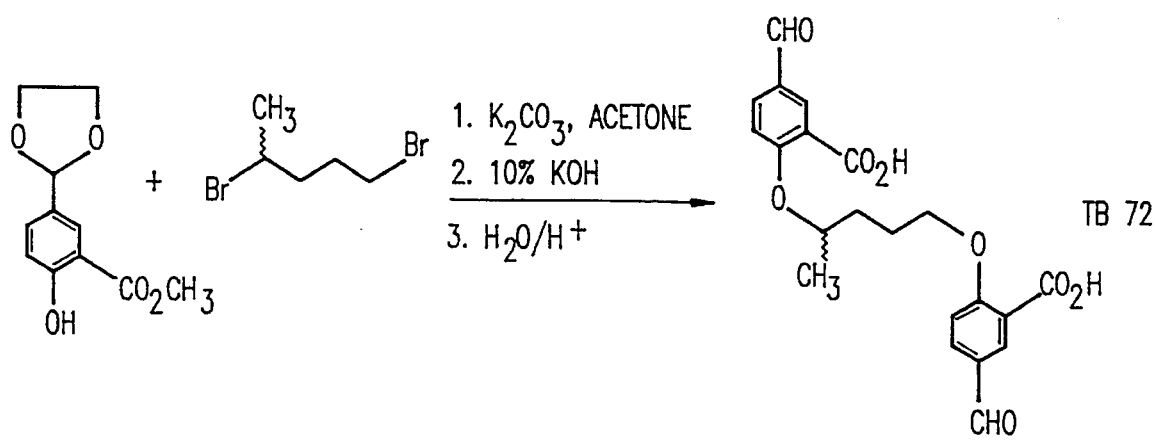

The synthesis of 1,5-bis(2-carboxy-4-formylphenoxy)-pentane, identified as compound TB57, is shown in FIG. 14. A mixture of methyl-2-hydroxy-5-acetalbenzoate (1.0g, 4.46 mmol), 1,5-dibromopentane (0.51 g, 2.23 mmol), and powdered potassium carbonate (2.0 g, 14.5 mmol) in dry 2-butanone were heated to reflux for 10 hours. The reaction mixture was filtered while hot and the solvent was removed under vacuum. The residue was flash chromatographed using hexane/ethyl acetate mixtures to obtain the desired intermediate diester. A mixture of the diester and 10% potassium hydroxide (30 mL) was heated to reflux for 30 minutes, the reaction mixture was filtered, cooled and acidified with concentrated hydrochloric acid. The precipitate was filtered, washed thoroughly with water (2×100 mL) and air dried to yield 0.61 g (68%) of the TB57 compound; mp 231° C. (dec.); $^1$HNMR (DMSO-$d_6$) δ 9.89 (s, 2H, CHO), 8.11 (d, 2H, ArH), 7.99 (dd, 2H, ArH), 7.29 (d, 2H, ArH), 4.15 (t, 4H, $CH_2O$), 1.80 (m, 4H, $CH_2$), 1.60 (m, 2H, $CH_2$). Analysis calculated for ($C_{21}H_{20}O_8$): C, 62.99; H, 5.04. Found: C, 62.78; H, 5.13.

EXAMPLE 19

The synthesis of 1,8-bis(2-carboxy-4-formylphenoxy)-octane, identified as compound TB58, is shown in FIG. 14. A mixture of methyl-2-hydroxy-5-acetalbenzoate (1.0 g, 4.46 mmol), 1,8-dibromooctane (0.61 g, 2.23 mmol) and powdered potassium carbonate (2.0 g, 14.5 mmol) in dry 2-butanone were heated to reflux for twelve hours. The reaction mixture was filtered while hot and the solvent was removed under vacuum. The residue was dissolved in ethyl acetate, washed with aqueous sodium hydroxid (0.5 M), dried (MgSO$_4$) and evaporated under reduced pressure to give a solid intermediate diester. A mixture of the diester and 10% aqueous potassium hydroxide (30ml) was heated to reflux for one hour, filtered, cooled, and acidified with concentrated hydrochloric acid. The precipitate was filtered, washed thoroughly with water (100 mL) and then with small amounts of diethyl ether. Air drying of the solid material yielded 0.75 g (90%); mp 213° C. (dec.); $^1$HNMR (DMSO-$d_6$) δ 9.89 (s, 2H, CHO), 8.11 (d, 2H, ArH), 7.99 (dd, 2H, ArH), 7.28 (d, 2H, ArH), 4.1 (t, 4H, $CH_2$), 1.70 (m, 4H, $CH_2$), 1.35 (m, 8H, $CH_2$). Analysis calculated for ($C_{24}H_{26}O_8$): C, 65.14; H, 5.93. Found: C, 64.96; H, 6.00.

EXAMPLE 20

The synthesis of 1,10-bis(2-carboxy-4-formylphenoxy)-decane, identified as compound TB73, is shown in FIG. 13. A mixture of methyl-2 -hydroxy-5-acetalbenzoate (1.0 g, 4.46 mmol), 1,10-dibromodecane (0.78 g, 2.23 mmol) and powdered potassium carbonate (2.0 g, 14.5 mmol) in dry 2-butanone were heated to reflux for 12 hours. The reaction mixture was filtered while hot and the solvent was removed under vacuum. The residue was dissolved in ethyl acetate, washed with aqueous sodium hydroxide (0.5 M), dried (MgSO$_4$) and evaporated under reduced pressure to give a solid intermediate diester. A mixture of the diester and 10% aqueous potassium hydroxide (30 ml) was heated to reflux for one hour, filtered, cooled and acidified with concentrated hydrochloric acid. The precipitate was filtered, washed thoroughly with water (100 mL) and then with small amounts of diethyl ether. Air drying of the solid material yielded 0.55 g (62%); mp 200° C. (dec.); $^1$HNMR (DMSO-$d_6$) δ 9.90 (s, 2H, CHO), 8.16 (d, 2H, ArH), 8.01 (dd, 2H, ArH), 7.31 (d, 2H, ArH), 4.15 (t, 4H, $CH_2$), 1.75 (m, 4H, $CH_2$), 1.22–1.49 (m, 12H, $CH_2$). Analysis Calculated for ($C_{26}H_{30}O_8$): C, 66.36; H, 6.44. Found: C, 66.18; H, 6.49.

EXAMPLE 21

The synthesis of 1,4-bis(2-carboxy-4-formylphenoxy)-pentane, identified as compound TB 72, is shown in FIG. 14. A mixture of methyl-2-hydroxy-5-acetalbenzoate (1.0 g, 4.46 mmol), 1,4-dibromopentane (0.78 g, 2.23 mmol) and powdered potassium carbonate (2.0 g, 14.5 mmol) in dry 2-butanone were heated to reflux for twelve hours. The reaction mixture was filtered while hot and the solvent was removed under vacuum. The residue was dissolved in ethyl acetate, washed with aqueous sodium hydroxide (0.5 M), dried (MgSO$_4$) and evaporated under reduced pressure to give a solid intermediate diester. A mixture of the diester and 10% aqueous potassium hydroxide (30 mL) was heated to reflux for one hour, filtered, cooled and acidified with concentrated hydrochloric acid. The precipitate was filtered, washed thoroughly with water (100 mL) and then with small amounts of diethyl ether. Air drying of the solid material yielded 0.42 g (45%); mp 191° C. (dec.); $^1$HNMR (DMSO-$d_6$) δ 9.90 (s, 2H, CHO), 7.90–8.39 (m, 6H, ArH), 7.11–7.10

(m, 4H, ArH), 5.55 (m, 1H, CH), 4.20 (t, 2H, $CH_2$), 2.40 (m, 2H, $CH_2$), 1.90 (m, 2H, $CH_2$), 1.62 (d, 3H, $CH_3$). Analysis Calculated for ($C_{21}H_{20}O_8$): C, 62.99; H, 5.05. Found: C, 63.22; H, 5.29.

EXAMPLE 22

Figure 15:
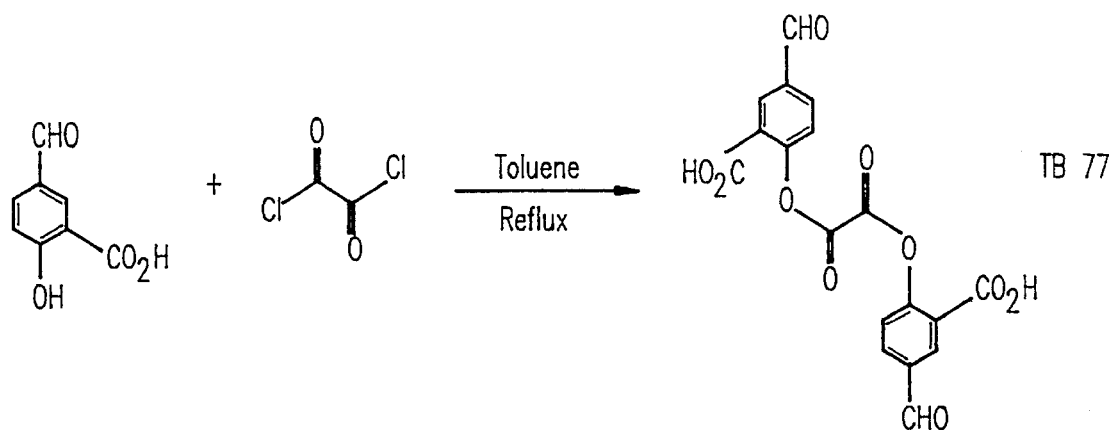
FIG. 15 is a chemical reaction scheme showing the synthesis of additional compounds according to the present invention.
Figure 15:
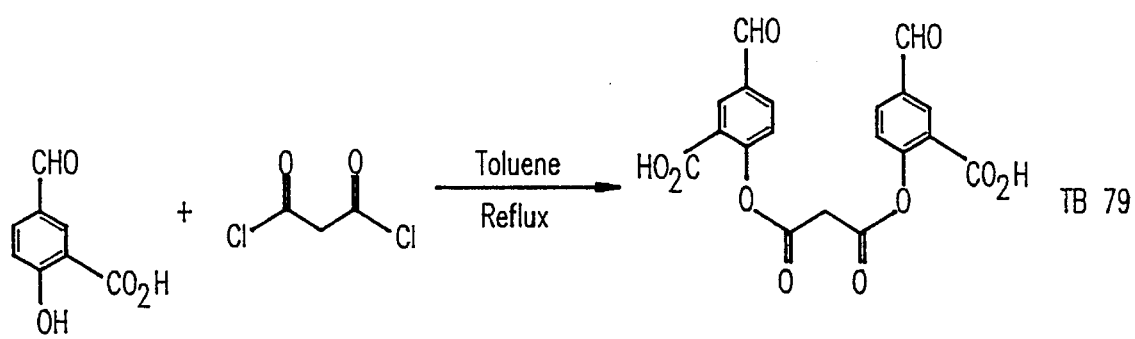
Figure 15:
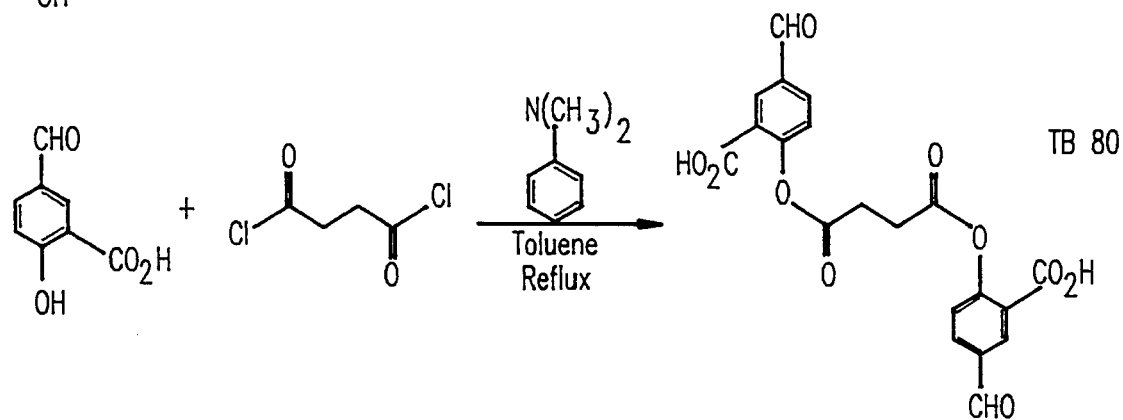
Figure 15:
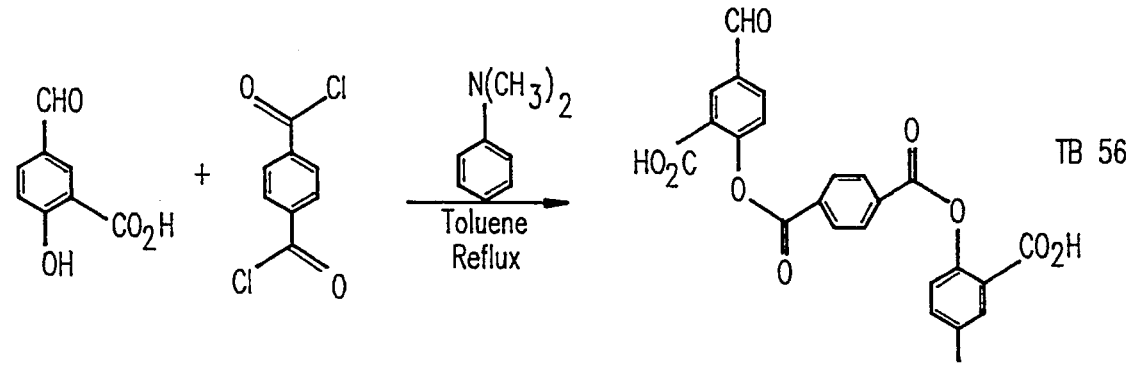

The synthesis of bis(2-carboxy-4-formylphenyl)-oxalate, identified as T577, is shown in FIG. 15. A solution of 5-formylsalicylic acid (1.66 g, 10 mmol) and oxalyl chloride (1.27 g, 10 mmol) in dry toluene (50 mL) was refluxed for twenty four hours and the solvent was removed in vacuo. The residues was dissolved in acetone (30 mL) and the product was precipitated by the addition of absolute ethanol. Recrystallization from acetone yielded the pure product (1.15 g, 59.5% yield); m.p. 182°–184° C.; $^1$HNMR (acetone-$d_6$) δ 13.01 (b, 2H, $CO_2H$), 10.1 (s, 2H, CHO), 8.52 (d, 2H, ArH), 8.22 (dd, 2H, ArH), 7.63 (d, 2H, ArH). Analysis Calculated for ($C_{18}H_{10}O_{10}$): C, 55.97; H, 2.62. Found: C, 55.84; H, 2.57.

EXAMPLE 23

The synthesis of bis(2-carboxy-4-formylphenyl)-malonate, identified as compound TB79, is shown in FIG. 15. A solution of 5-formylsalicylic acid (1.66 g, 10 mmol) and malonyl chloride (1.41 g, 10mmol) in dry toluene (50 mL) was refluxed for twenty four hours. The mixture was cooled to room temperature and the product was filtered and washed with warm toluene. Recrystallization from ethyl acetate/toluene yielded the pure product (1.55 g, 81% yield); m.p. 205°–207° C. (dec.); $^1$HNMR (acetone-$d_6$) δ 12.89 (b, 2H, $CO_2H$), 9.91 (s, 2H, CHO), 8.52 (d, 2H, ArH), 8.23 (dd, 2H, ArH), 7.63 (d, 2H, ArH) (s, 2H, $CH_2$). Analysis Calculated for ($C_{19}H_{12}O_{10}$): C, 54.00; H, 3.03. Found: C, 54.12; H, 2.98.

EXAMPLE 24

The synthesis of bis(2-carboxy-4-formylphenyl)-succinate, identified as compound TB80, is shown in FIG. 15. To a solution of succinyl chloride (1.55 g, 10 mmol) in dry toluene (80 ml) was added 5-formylsalicylic acid (3.32 g, 20 mmol) and N,N-dimethylaniline (4.84 g, 40 mmol), and the mixture was stirred for four hours at 25° C. Water (60 mL) and concentrated hydrochloride acid (15 mL) were added and the mixture was stirred for twenty minutes and filtered. The solid product was washed twice with cold water and recrystallized from dioxane/water to yield the desired product (4.6g, 64%); m.p. 218°–220° C.; $^1$HNMR (DMSO-$d_6$) δ 9.89 (s, 2H, CHO), 8.53 (d, 2H, ArH), 8.23 (dd, 2H, ArH), 7.63 (d, 2H, ArH), 2.9 (s, 4H, $CH_2$). Analysis Calculated for ($C_{20}H_{14}O_{10}$): C, 57.93; H, 3.41. Found: C, 57.76; H, 3.38.

EXAMPLE 25

The synthesis of bis(2-carboxy-4-formylphenyl)-fumerate, identified as compound TB40, is shown in FIG. 15. To a solution of fumeryl chloride (1.53 g, 10 mmol) in dry toluene (50 ml) was added 5-formylsalicylic acid (1.66 g, 10 mmol) and N,N-dimethylanaline (2.4 g, 20 mmol), and the mixture was stirred overnight at 25° C. Water (30 mL) and concentrated hydrochloride acid (5 mL) were added and the mixture was stirred for twenty minutes and filtered. The solid product was washed twice with cold water and recrystallized from acetone/hexane to yield 1.32 g (64%) of the desired product; m.p. 180°–182° C.; $^1$HNMR (DMSO-$d_6$) δ 10.1 (s, 2H, CHO), 8.53 (d, 2H, ArH), 8.23 (dd, 2H, ArH), 7.63 (d, 2H, ArH), 7.28 (s, 2H, CH=CH). Analysis Calculated for ($C_{20}H_{12}O_{10}$·$H_2O$): C, 55.82; H, 3.28. Found: C, 55.70; H, 3.27.

EXAMPLE 26

The synthesis of bis(2-carboxy-4-formylphenyl)-terephthalate, identified as compound TB56, which is shown in FIG. 15. To a solution of terephthaloyl chloride (2.03 g; 10 mmol) in dry toluene (50 mL) was added 5-formylsalicylic acid (3.32 g, 20 mmol) and N,N-dimethylaniline (2.4 g, 20 mmol), and the mixture was stirred overnight at 25° C. Water (30 mL) and concentrated hydrochloride acid (5 mL) were added and the mixture was stirred for twenty minutes and filtered. The solid product was washed twice with cold water and recrystallized from acetone/water to yield 3.20 g (69.2%) of the desired product; m.p. 209°–211° C.; $^1$HNMR (DMSO-$d_6$) δ 9.91 (s, 2H, CHO), 8.53 (d, 2H, ArH), 8.23 (dd, 2H, ArH), 7.63 (d, 2H, ArH), 7.55 (dd, 4H, ArH). Analysis Calculated for ($C_{24}H_{14}O_{10}$): C, 62.34; H, 3.06. Found: C, 62.42; H, 3.19.

EXAMPLE 27

Table 1 shows the $P_{50}$ of both the control experiments ($P_{50}C$) as well as the drugs ($P_{50}D$) wherein the change in the $P_{50}$ is defined as $\Delta P_{50}=P_{50}D-P_{50}C$. Table 2 shows the $P_{50}D$, $P_{50}C$, and $\Delta P_{50}$ for studies conducted with TB17, TB18, and TB19 in whole blood.

TABLE 1

| EFFECT OF DRUG COMPOUNDS ON THE OXYGEN AFFINITY OF HEMOGLOBIN SOLUTIONS | | | |
| --- | --- | --- | --- |
| Name of Compound | $P_{50}C$ (aver.) | $P_{50}D$ (aver.) | $\Delta P_{50}$ |
| 5-formylsalicylic acid (MS1) | 22.0 | 21.0 | 1.0 |
| 4-carboxybenz-aldehyde (MS2) | 23.0 | 21.0 | 2.0 |
| 5-formylaspirin (TB8) | 22.0 | 21.0 | −1.0 |
| 2-benzyloxy-5-formylbenzoic acid (TB32) | 20.0 | 18.0 | −2.0 |
| 1-[(2-carboxy-4-formylphenoxy)]-4-[4-carboxyphenoxy)] butane (TB35) | 21 | 25 | 4 |
| a-(2-carboxy-4-formylphenoxy)-p-toluic acid (TB34) | 20.0 | 14.0 | −6.0 |
| bis(2-carboxy-4-formylphenoxy)methane (TB62/45) | 22.0 | 51.0 | 29.0 |
| 1,2-bis(2-carboxy-4-formylphenoxy)-ethane (TB63/41) | 22.0 | 46.0 | 24.0 |
| 1,3-bis(2-carboxy-4-formylphenoxy)-propane (TB36) | 22.0 | 44.0 | 22.0 |
| 1,4-bis(2-carboxy-4-formylphenoxy)-butane (TB19) | 22.0 | 42.0 | 20.0 |
| 1,5-bis(2-carboxy-4-formylphenoxy)-pentane (TB57) | 22.0 | 33.0 | 11.0 |
| 1,6-bis(2-carboxy-4-formylphenoxy)-hexane (TB42) | 22.0 | 39.0 | 17.0 |
| 1,8-bis(2-carboxy-4-formylphenoxy)-octane (TB58) | 22.0 | 37.0 | 15.0 |
| 1,10-bis(2-carboxy-4-formylphenoxy)-decane (TB73) | 22.0 | 33.0 | 11.0 |

TABLE 1-continued

EFFECT OF DRUG COMPOUNDS ON THE OXYGEN AFFINITY OF HEMOGLOBIN SOLUTIONS

| Name of Compound | $P_{50}C$ (aver.) | $P_{50}D$ (aver.) | $\Delta P_{50}$ |
|---|---|---|---|
| α,α-bis(2-carboxy-4-formylphenoxy)-butene (TB18) | 22.0 | 40.0 | 18.0 |
| 1,4-bis(2-carboxy-4-formylphenoxy)-pentane (TB72) | 22.0 | 30.0 | 8.0 |
| α,α-bis(2-carboxy-4-formylphenoxy)-o-xylene (TB5) | 21.5 | 31.0 | 9.5 |
| α,α-bis(2-carboxy-4-formylphenoxy)-m-xylene (TB10) | 21.5 | 26.0 | 4.5 |
| α,α'-bis(2-carboxy-4-formylphenoxy)-p-xylene (TB11) | 21.5 | 24.0 | 2.5 |
| Bis(2-carboxy-4-formylphenyl)-fumerate (TB40) | 20.0 | 14.0 | −6.0 |
| Bis(2-carboxy-4-formylphenyl)-oxalate (TB77) | 21.0 | 19.5 | −1.5 |
| Bis(2-carboxy-4-formylphenyl)-malonate (TB79) | 21.0 | 19.0 | −2.0 |
| Bis(2-carboxy-4-formylphenyl)-succinate (TB80) | 20.0 | 14.5 | −5.5 |
| Bis(2-carboxy-4-formylphenyl)-terephthalate (TB56) | 20.0 | 16.0 | −4.0 |

TABLE 2

WHOLE BLOOD STUDIES WITH TB17, TB18, AND TB19

| Cpd. | $P_{50}C$ | $P_{50}D$ (aver.) | $\Delta P_{50}D$ |
|---|---|---|---|
| TB17 | 25.0 | 14.5 | −9.5 |
| TB18 | 25.0 | 19.0 | −6.0 |
| TB19 | 25.0 | 19.5 | −5.5 |

The compounds that shift the hemoglobin oxygen equilibrium curve to the left may be useful as antisickling agents. Left-shifting agents usually stabilize the more soluble oxy form of Hb relative to the deoxy form.

Those compounds which right-shift the curve may be useful for treating ischemia, in blood storage, in wound healing, in radiotherapy, and for use in antilipidemic therapy.

As indicated in Table 2, TB17, TB18, and TB19 all left shift whole blood solution even though they right shift hemoglobin solution. The source of this apparent discrepancy is clarified in Rosenthal et al., 1975, *J. Invest. Radiol.* When added to whole blood, these compounds may alter the ionic distribution by virtue of their osmotic effect, where intracellular pH rises and $P_{50}$ falls. These compounds may act directly with hemoglobin in solution and decrease affinity ($P_{50}$ rises) proportional to the concentration present.

EXAMPLE 28

X-ray diffraction analyses were used to study several of the new drug complexes including MS1, MS2, TB8, TB10, TB17, TB19, TB32, TB36, TB62, and TB63. The difference electron-density maps of all complexes discussed are that of the HbA tetramer/drug molar ratio of 1:5, except TB17 which is 1:10. All drug molecules contain at least two functionalities, an aldehyde and a carboxylate, common to all of them. The difference electron-density maps of all complexes showed binding in the α cleft water cavity, the aldehyde functional group forms a covalent linkage with the amino group of the Val-α, while the two carboxylate oxygens are involved in a network of electrostatic (ionic) and/or hydrogen bonding with the symmetry related guanidium group of the Arg-141α residue. The only exception was MS2 where only one of the carboxylate oxygens was involved in the salt bridge interaction. The above binding site, which is common to all of the complexes, will be referred to as the α-cleft binding site. Some of the above drug compounds have additional functional groups which are also involved in additional interaction with other HbA residues, including hydrogen bonding, van der Waals interaction, and a second covalent bonding.

All complexes have two molecules of the drug compounds bound at the above-mentioned α-cleft site and are related by the two fold noncrystallographic axis. These sites are further noted as the α1-cleft site (Val-1α1 binding site), and the α2-cleft site (Val-1α2 binding site). In all complexes, the electron density at the α2-cleft site were slightly bigger and better defined than the electron density at the α1-cleft site. In addition to the binding at the α-cleft site, some of the drug compounds also bind to other secondary sites, including other sites in the α-cleft water cavity, the β-cleft water cavity located at Val-1β, and the Hb polymer contact site located near the residues His-116β and His-117β.

5-Formylsalicyclic acid (MS1)

The difference electron-density map of the HbA/MS1 complex indicated four binding sites for MS1 in the central water cavity of HbA. The two major binding sites, which are symmetry-related, are in the α-cleft binding site. The other two minor binding sites are in the β-cleft, which are also symmetry-related. The β-cleft binding sites have lower electron densities than the α-cleft binding sites. A fit of a model of MS1 to the symmetry-related electron-density map at the a-cleft sites showed the Val-1α N-terminal amino atom extending into the MS1 density indicating a covalent binding involving the aldehyde of MS1 and the amino nitrogen of the Val-1α to form a Schiff base adduct. The carboxylate of the MS1 molecule extends through the molecular diad to form a network of electrostatic and hydrogen bonding with the symmetry-related guanidinium group of Arg-141α. The hydroxyl of MS1 hydrogen bonds with the hydroxyl group of Thr-134α. There were various other contacts between the drug and the Hb residues in the two symmetry-related α-cleft binding sites, the shortest was the contact between the b carbon of Ala-130, and C9, O8 and O11 of MS1 which are within 3.0–3.8A. There were positive and/or negative peaks found on/or around these globin residues, Val-1α, Arg-141α, Thr-134α, Lys-127α, Ala-130α, and Ser-131α indicating movements. The two minor symmetry-related β-cleft binding sites had lower electron-density occupancies and only one site, at the β1-subunit could be approximately fit with a model of MS1 molecule. The electron-density at the β2-subunit site is very low and poorly defined, no attempt was made to fit the MS1 molecule there. The fit of MS1 to the electron-density contours at the β1-subunit indicates MS1 has bound to Val-1β to form a schiff base adduct. The carboxylate forms a salt bridge with the amino group of Lys-82β, the hydroxyl group forms a hydrogen bonding with the amide nitrogen of the Ala-140β. Large negative densities on the Val-1β, Lys-81β, and Leu-82β indicate movement of these residues.

4-Carboxybenzaldehyde (MS2)

The difference electron-density map of the HbA/MS2 complex indicated binding exclusively at the two symmetry-related α-cleft sites. There is apparent covalent linkage between the drug and the terminal amino nitrogen of Val-1α to form a schiff base adduct. The carboxylate of the drug is disposed towards the guanidinium groups of the symmetry-related Arg-141a and forms a weak electrostatic interaction compared to that of the MS1 complex. There were no other apparent binding sites. There were positive and/or negative peaks found on/or around these globin residues: Val-1α, Thr-134α, Lys-127α, and Ser-131α, Val-132α, and Arg-141α, indicating movements.

5-Formylaspirin (TB8)

The difference electron-density map of the HbA/TB8 complex showed binding of TB8 at the two symmetry-related α-cleft sites of Val-1α, the same place the MS1 molecules bind. The electron-density contour for the complex was similar in shape, and orientation to those observed for that of MS1. This indicates loss of the acetyl functional group, and only the MS1 analog is left for binding. A fit of the MS1 analog to the electron-density contour also confirms that the binding molecule is without the acetyl functional group. As observed for MS1, the aldehyde forms a Schiff base adduct with the terminal amino nitrogen of Val-1α, the carboxylate then extends through the molecular diad to form a network of electrostatic and hydrogen bonding with the symmetry-related guanidinium group of the Arg-141α. The salt bridge strength is comparable to the one in the MS1 complex. The hydroxyl also forms hydrogen bonding with the hydroxyl of Thr-134α. The acetyl functional group was not apparent in the electron-density map. The shortest contact is between the B carbon of Ala-130α, and C9, O8 and O11 of TB8 which are within 2.9–3.3 A. Shown are other close contacts between the TB8 and the globin residues in the a-cleft binding site. There are positive and/or negative peaks found on/or around these globin residues, Val-1α, Thr-134α, Lys-127α, and Ser-131α indicating movements. Very large negative electron-density found at the two symmetry-related β-cleft binding sites, and very little positive electron-density found only at the β1-site, may seem to indicate possible drug binding at the β-sites. The positive electron-density at the B-cleft sites of TB8 complex were much smaller than found with the MS1 complex, and none of the TB8 B-cleft sites could be fit with the drug molecule.

2-Benzyloxy-5-Formylbenzoic Acid (TB17)

The difference electron-density map of the HbA/TB17 complex showed three molecules of TB17 reacted to the Hb tetramer. Two of the molecules bind at the two symmetry-related α-cleft sites, representing the major binding sites. A third of the molecule was determined to bind across the two Lys-99α residues, representing a minor binding site. A fit of a model of TB17 to the symmetry-related electron densities at the two major α-cleft binding sites showed the compound to form both covalent and network of electrostatic and hydrogen bondings as described for MS1 and TB8. However, the salt bridge network was quite stronger than found in MS1 or TB8 as indicated by the bonding distances. The fit of the molecule demonstrated the phenyl substituents for the two drug molecules were further down the water channel, with distance of 3.0 to 3.9 A to the residues of Thr-134α and Thr-137α. Other short contacts are between the ether oxygen (O11) of TB17 and B carbon of Ala-130α which is 2.8 A. Positive and/or negative electron densities were observed on/or around these globin residues: Val-1α, Thr-134α, Lys-127α, and Ser-131α, which indicates movements. The minor binding site, which was indicated by a smaller electron-density, had density stretching between the two symmetry-related Lys-99α residues. An approximate fit of the drug in the density shows a covalent linkage between the amino nitrogen of Lys-99α1, and an electrostatic interaction between the carboxylic acid group and the amino nitrogen of the Lys-99α2 residue. The phenyl substituent is disposed, such that it closest contacts are with the residues Lys-99α2, Asn-108β1, and Leu-100α1, with distances of 3.6, 4.2, and 3.8 A respectively. Positive and/or negative electron densities detected on/or around these globin residues, Lys-99α, and Leu-100α indicated movements.

1,3-Bis(2-Carboxy-4-Formylphenoxy)-Propane (TB36)

The difference electron-density map of the HbA/TB36 complex indicated binding exclusively at the two symmetry-related α-cleft sites. In addition to the apparent covalent and salt bridge bondings as already described above for the MS1 complex, the fit of a model of TB36 molecule to the electron-density indicated a second covalent bonding between the second aldehyde group of the drug and the amino nitrogen of the Lys-99α residue. The Val-1α and Lys-99α which are involved in the covalent bonding with the same TB36 molecule are found on symmetry-related α-subunit, the Arg-141α which is involved in the salt bridge interaction is found on the same α-subunit as the Lys-99α. There were various contacts between the drug and the Hb residues determined in the binding sites, the shortest was the contact between the B carbon of Ala-130α, and O11 of TB36 which is about 3.1 A apart. There were positive and/or negative peaks found on/or around these globin residues indicating movements: Val-1 1α, Arg-141α, Thr-134α, Lys-127α, Ala-130α, Ser-131α, Pro-95α, Val-96α, Lys-99α, and Thr-137α. There was a large negative electron-density peak found between the two phenyl groups (the phenyl groups disposed towards the Lys-99α residues) of the TB36 drugs. The plane of the two phenyl rings relative to each other was almost parallel. The closest distance between the two phenyl ring planes was 4.0 A. The second acid groups which are on the phenyl rings were determined to have a closest distance of 3.9 A to Pro-95α.

1,4-Bis(2-Carboxy-4-Formylphenoxy)-Butane (TB19)

Like the difference electron-density map of the HbA/TB36 complex, that of HbA/TB19 complex indicated binding exclusively at the two symmetry-related α-cleft sites, and it had similar bonding properties as discussed above for TB36. TB19, which is a carbon chain longer than TB36, showed a breakage in the electron-density map in the middle of the molecule. Also the electron-density was slightly longer than found with the TB36 complex. There were various contacts between the drug and the Hb residues in the two binding sites, and the shortest was the contacts between the α and α carbon of Ala-130α and O11 of TB19 which was 2.8 A apart. There were positive and/or negative peaks found on/or around these globin residues indicating movements: Val-1α, Thr-134α, Lys-127α, Ala-130α, Ser-131α, Pro-95α, Val-96α, and Lys-99α. Like the difference electron-density map of the HbA/TB36 complex, there was also a large negative electron-density peak between the two phenyl groups (the phenyl groups disposed towards the Lys-99α residues) of the TB19 drugs. The phenyl rings were almost parallel to each other. The closest distance between the two phenyl ring planes is 4.5 A. Also the second carboxylic acid groups which were on the phenyl rings were not involved in any apparent bonding, their closest distance to any globin residues are over 4.5 A.

α,α-Bis(2-carboxy-4-formylphenoxy)m-xylene (TB10)

The difference electron density map of the HbA/TB10 complex in the α-cleft binding site, was quite similar to that of HbA/TB19 complex, with similar bonding properties as discussed above for TB36. Like the electron-density of the TB19 complex, TB10 which is a carbon chain longer than TB19, also showed a breakage in the electron-density map in the middle of the molecule. Small but pieces of electron densities confined to the β-cleft site, near the two Val-1β and the Lys-82β, were observed and may indicate a third binding site for a molecule of TB10. The TB10 compound could not be fit in the electron-density at this site. There were various contacts between the drug and the Hb residues in the two α-cleft binding sites, the shortest were the contacts between the β carbon of Ala-130α and O11 of TB10 which is 2.4 A. There were positive and/or negative peaks found on/or around these globin residues indicating movements: Val-1α, Thr-134α, Lys-127α, Ala-130α, Ser-131α, Pro-95α, Val-96α, and Lys-99α. Like the difference electron-density map of the HbA/TB36 complex there was also a large negative peak between the two phenyl groups (the phenyl groups disposed towards the Lys-99α residues). The closest distance between the two phenyl ring planes was 5.7 A. Also, the second carboxylic acid groups which are on the phenyl rings have a closest distance of 3.5 A to Trp-37β.

Bis(2-carboxy-4-formylphenoxy)-methane (TB62)

The difference electron density map of HbA/TB62 complex indicates binding exclusively at the two symmetry-related α-cleft sites, and has similar bonding properties as discussed above for TB36. Unlike TB36 and the other dialdehyde complexes, the second carboxylic group which is further down the water cavity is in close contact with Thr-134α. The two oxygens are 2.4 and 2.9A from the hydroxide of the Thr-134α. There are other contacts between the drug and the Hb residues in the binding sites, where the shortest contact between the β carbon of Ala-130α, and O11 of TB62 which is about 3.3 A apart. There are positive and/or negative peaks found on/or around these globin residues indicating movements: Val-1α, Arg-141α, Thr-134α, Lys-127α, Ala-130α, Pro-95α, Val-96α, and Lys-99α. The closest distance between the two phenyl ring planes is 2.9A.

1,2-Bis(2-carboxy-4-formylphenoxy)-ethane (TB63)

The difference electron-density map of the HbA/TB63 complex indicates binding exclusively at the two symmetry-related α-cleft sites, and has similar bonding properties as discussed above for TB62. Like TB62, the second carboxylic group which is further down the water cavity is also in close contact with Thr-134α. The carboxylic oxygens are 2.3 and 3.7 A from the hydroxide of the Thr 134α. The N, β, and α carbons of the Thre-134α are also in close contact with the carboxylate with distances ranging between 3.0 and 3.8A. The β carbon of Ala-130α and O11 of TB62 is about 3.4 A apart. There are positive and/or negative peaks found on/or around thes globin residues indicating movements: Val-1α, Arg-141α, Thr-134α, Lys-127α, Ala-130α, Pro-95α, Val-96α, Lys-99α, and Thr-137α. The closest distance between the two phenyl ring planes is 5.5 A.

As discussed above, the dialdehyde compounds that covalently crosslink the n-terminal valine amino group one α-chain with the ε-amino group of Lys 99 of the opposite α-chain (as well as the symmetry related site) may be useful for stabilizing blood products or blood substitutes.

Table 3 summarizes the crystallographic data obtained for the synthesized compounds.

TABLE 3

| | | Crystalographic Data. | | | | | | |
|---|---|---|---|---|---|---|---|---|
| | | | Cell Dimensions | | | $d_{lim}$,[a] | $R_{int}$ or $R_{imerge}$,[b] | $R_{d-n}$,[c] |
| Compound Added to HbA | [Cpd]/[HbA] | (a, | b, | c)/A, | β, deg | A | % | % |
| 5-Formylsalicyclic Acid (MS1)[d] | 5 | 63.20 | 83.48 | 53.83 | 99.57 | 1.94 | 5.9 | 10.4 |
| 4-Carboxybenzaldehyde (MS2)[e] | 5 | 63.26 | 83.65 | 53.78 | 99.88 | 3.0 | 6.0 | 9.5 |
| 5-Formylaspirin (TB8)[d] | 5 | 63.25 | 83.60 | 53.79 | 99.40 | 1.94 | 6.6 | 11.0 |
| 2-Benzyloxy-5-Formylbenzoic Acid (TB17)[d] | 10 | 63.16 | 83.44 | 53.97 | 99.44 | 1.94 | 6.7 | 12.5 |
| 1,4-Bis(2-Carboxy-4-Formylphenoxy)-Butane (TB19)[d] | 5 | 63.24 | 83.40 | 53.83 | 99.38 | 1.94 | 5.7 | 9.5 |
| α,α'-Bis(2-Carboxy-4-Formylphenoxy)-m-Xylene (TB10)[d] | 5 | 63.24 | 83.51 | 53.90 | 99.40 | 1.94 | 5.3 | 10.4 |
| 1,3-Bis(2-Carboxy-4-Formylphenoxy)-Propane (TB36)[d] | 5 | 63.28 | 83.55 | 53.81 | 99.53 | 1.94 | 4.5 | 9.3 |
| -Phenethyloxy-5-Formylbenzoic Acid (TB32)[d] | 5 | 63.31 | 83.61 | 53.86 | 99.39 | 1.94 | 5.4 | 11.6 |
| Bis(2-Carboxy-4-Formylphenoxy)-Propane (TB62)[d] | 5 | 63.17 | 83.55 | 53.82 | 99.47 | 1.94 | 4.8 | 9.6 |
| 1,2-Bis(2-Carboxy-4-Formylphenoxy)-Propane (TB63)[d] | 5 | 63.17 | 83.51 | 53.77 | 99.42 | 1.94 | 5.3 | 9.8 |

[a]$d_{lim}$ is the radius of limiting sphere in which data were collected.
[b]$R_{int}$ is the agreement factor of intensities between Friedel pairs within each set of diffractometer data; $R_{int} = \Sigma_{hkl}(II_{hkl} - I_{h-kl}|)/\Sigma_{hkl}(I_{hkl})$, and $R_{merge}$ is the consistency of equivalent reflection between the entire R-Axis IIC image plate data set; $R_{merge} = \Sigma\Sigma|F^2(i)/G(i) - <F^2(h)>|/\Sigma\Sigma F^2(i)/G(i)$.
[c]$R_{d-n}$ is the agreement factor of structure amplitudes between native and derivative data; $R_{d-n} = \Sigma_{hkl}|(|F_d| - |F_n|)|/\Sigma_{hkl}|F_d|$.
[d]Data set from R-axis IIC image plate.
[e]Data set from diffractometer.

The above results indicate that a number of new aldehydic agents can bind within the water cavity of hemoglobin and cross-link the two α subunits. The new compounds generally will either (1) bind the n-terminal valine of one α subunit and the lysine 99 and arginine 141 of the other α subunit, or (2) bind the n-terminal valine of one α subunit and the arginine 141 of the other α subunit. In either case, the binding is stereospecific and, often, two of the compounds will be bound between the two α subunits.

The first group of compounds can be defined structurally as follows:

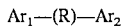

wherein $Ar_1$ and $Ar_2$ are aryl groups which are substituted with one or more moieties selected from the group consisting of aldehydes and carboxylic acids, and R is a sequence which contains moieties selected from the group consisting of saturated and unsaturated carbon atoms, oxygen atoms, and aromatic moieties. A particularly preferred compound according to this embodiment will have the following structure:

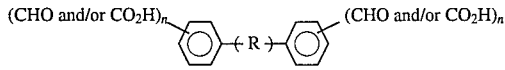

where n is 1 or more, whereby each phenyl is substituted with at least one aldehyde or carboxylic acid. Carboxylic acid moieties tend to increase the solubility of the molecule in blood substitute preparations relative to aldehyde moieties; however, the carboxylic acid moities make the compounds more difficult to penetrate into red cells.

The second group of new compounds can be defined as follows:

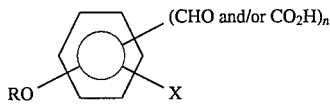

wherein n is 2 or more, whereby each phenyl is substituted with at least two functional groups selected from the group consisting of aldehydes and carboxylic acids, wherein X is selected from the group consisting of hydrogen or hydroxy moieties, and wherein R is a sequence which includes aliphatic and aromatic moieties connected to the oxygen by an ester or ether linkage.

FIGS. 1, 4, and 5 identify several binding sites identified in the hemoglobin molecule. It has been discovered that by crosslinking the two α subunits, the hemoglobin molecule can be allosterically modified for a higher or lower oxygen carrying capacity. While the compounds described above have the aldehyde and carboxylic acid moities bonded directly to the phenyl group, it should be understood that minor variations such as having the aldehyde or carboxylic acid on short (1–5 carbon aliphatic chains) could also produce similar results.

While the invention has been described in terms of its preferred embodiments, those skilled in the art will recognize that the invention can be practiced with modification within the spirit and scope of the appended claims.

We claim:

1. A compound sized to interact inside a central water cavity of a hemoglobin molecule and bridge two α subunits of said hemoglobin molecule, said compound having at least three functional groups wherein each functional group is selected from the group consisting of aldehydes and carboxylic acids, a first functional group being positioned on said compound to bond with an n-terminal Valine 1 on a first α subunit, and a second functional group being positioned on said compound to bond with Arginine 141 on a second α subunit, a third functional group being positioned on said compound to bond with Lysine 99 on said second α subunit, said compound having a chemical structure selected from the group consisting of:

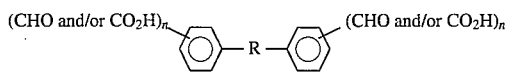

where n is at least 1, and R is a sequence which contains moieties selected from the group consisting of saturated and unsaturated carbon atoms, oxygen atoms, and aromatic moieties.

2. The compound of claim 1 wherein the chemical structure is selected from the group consisting of:

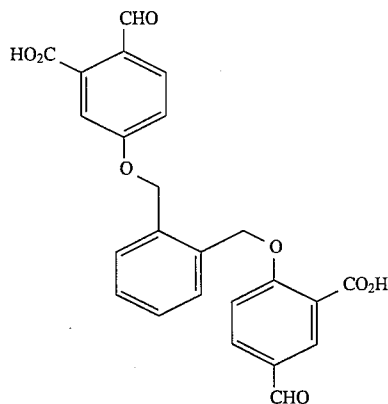

TB 5

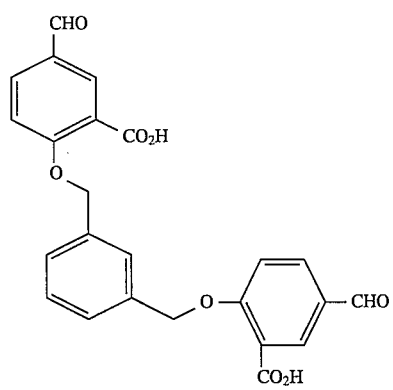

TB 10

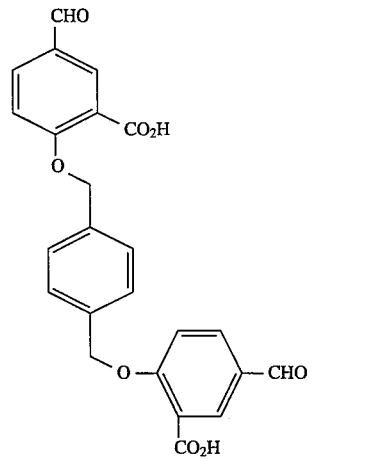

TB 11

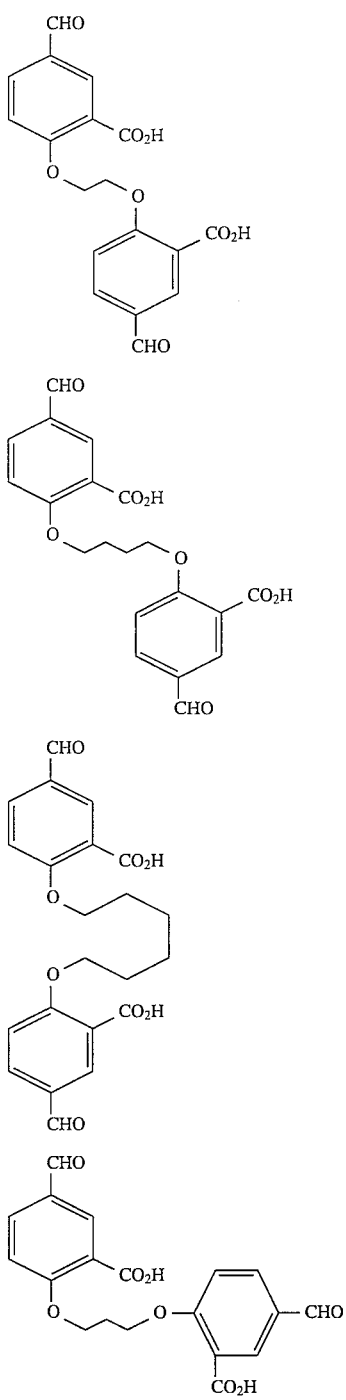
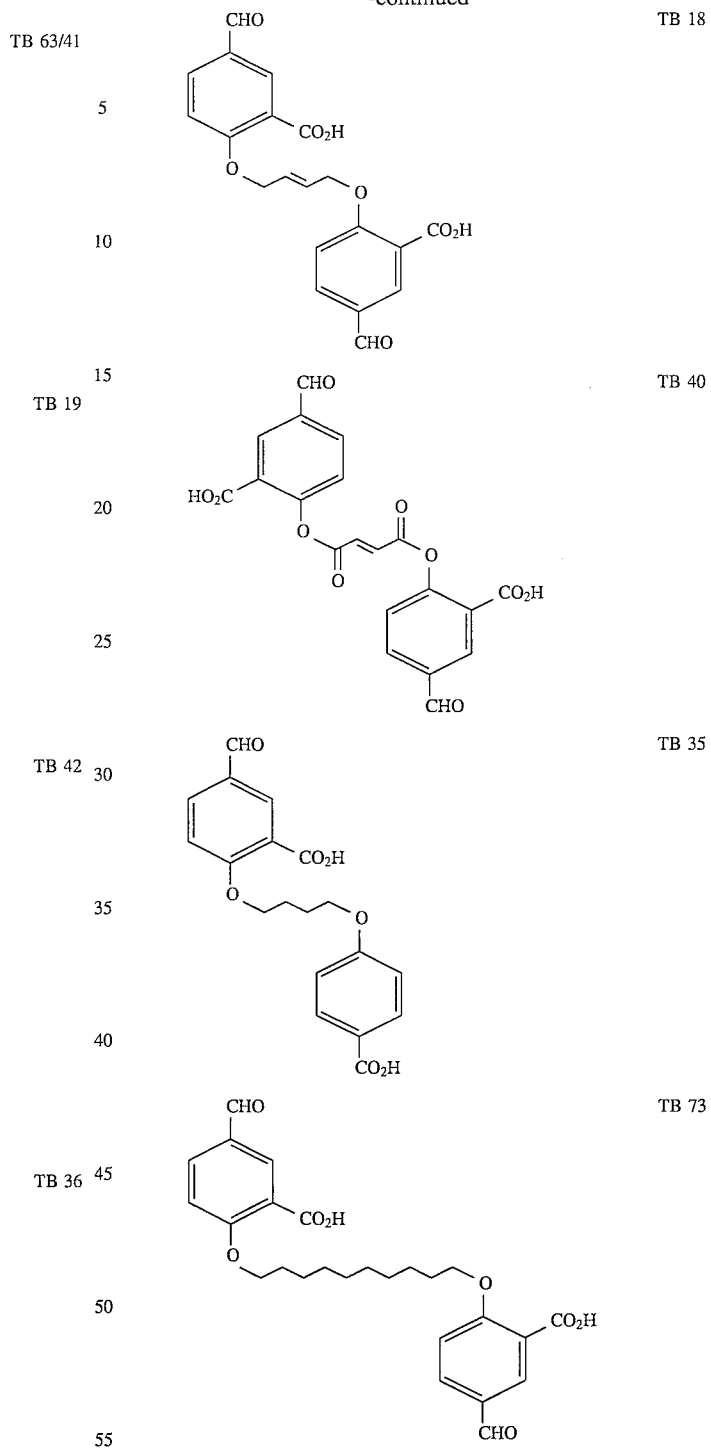

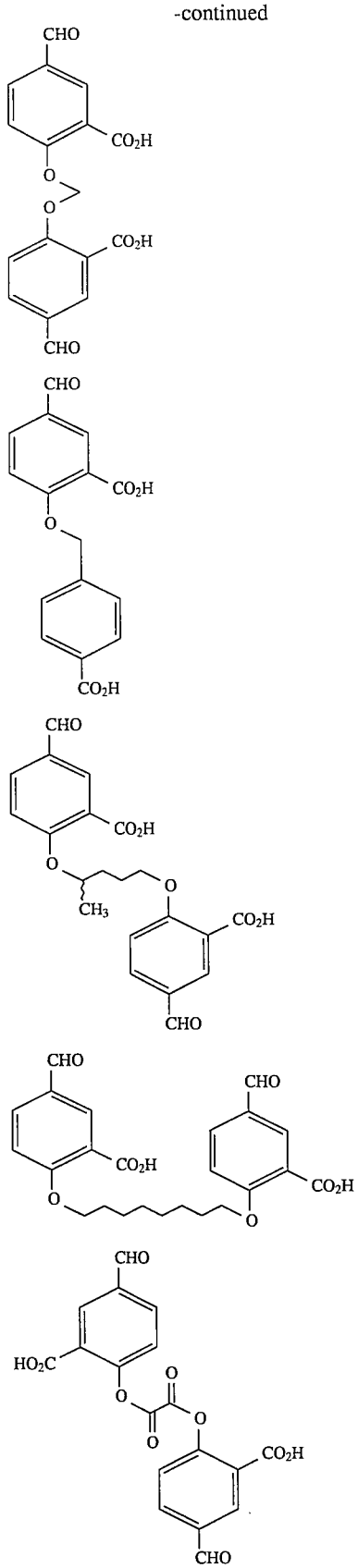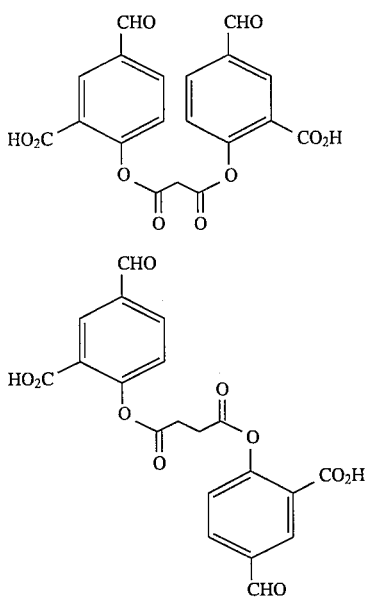

3. A compound wherein the chemical structure is selected from the following group:

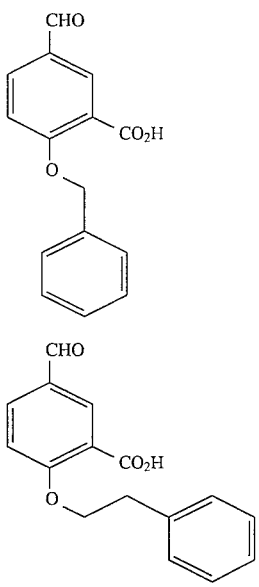
TB 17

TB 32

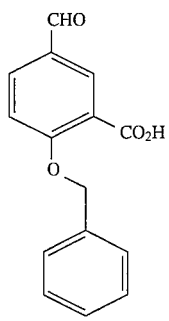
TB 17

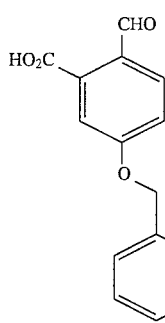
TB 5

4. A method for allosterically modifying hemoglobin, as comprising the steps of:

exposing hemoglobin to a compound which interacts inside the central water cavity of hemoglobin and bridges the two α subunits, said compound having at least two function groups wherein each function group is selected from the group consisting of aldehydes and carboxylic acids, a first functional group being positioned to bond with the n-terminal Valine 1 on a first α subunit, a second functional group being positioned to bond with Arginine 141 on a second α subunit, said compound having a chemical structure selected from the group consisting of:

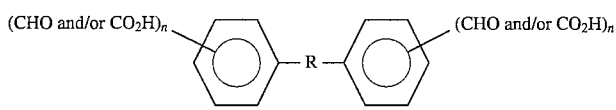

and

where n is at least 1, and R is a sequence which contains moieties selected from the group consisting of saturated and unsaturated carbon atoms, oxygen atoms, and aromatic moieties: and allowing said compound to interact inside the central water cavity of hemoglobin and bridge the two α subunits.

5. The method of claim 4 wherein said compound includes a third functional group selected from the group consisting of aldehydes and carboxylic acids, said third functional group being positioned on a phenyl ring of said compound to bond with Lysine 99 on said second α subunit.

6. The method recited in claim 4 wherein said compound has a chemical structure selected from the group consisting of:

-continued

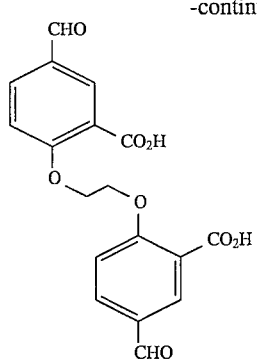
TB 63/41

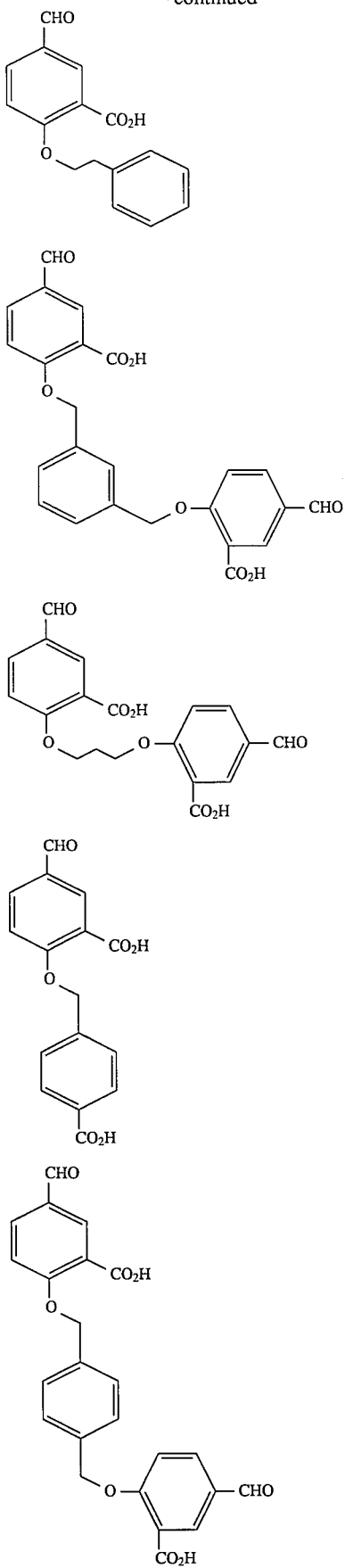
TB 32
TB 10
TB 36
TB 34
TB 11
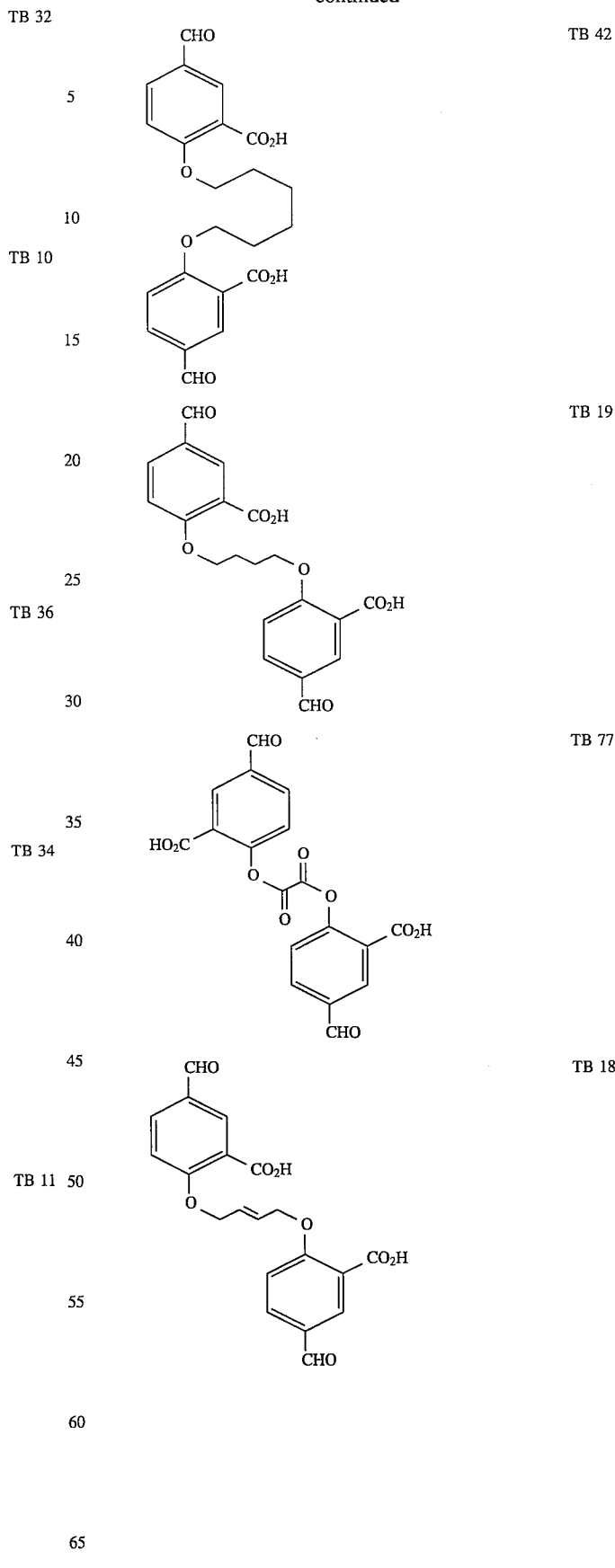
TB 42
TB 19
TB 77
TB 18

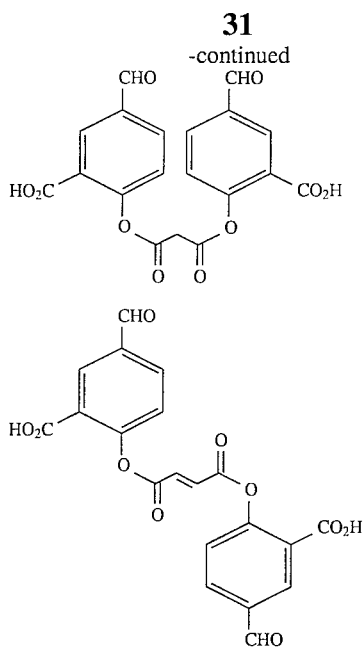
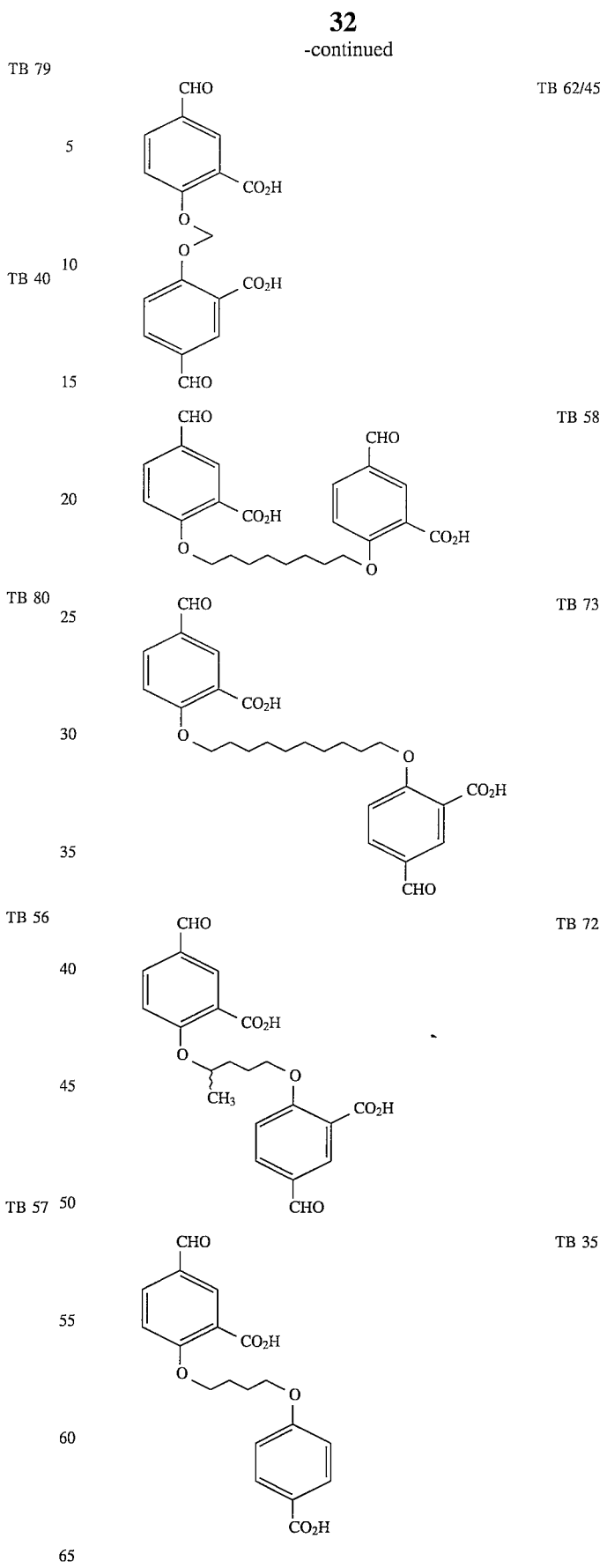

7. The compound of claim 1 wherein the chemical structure is:

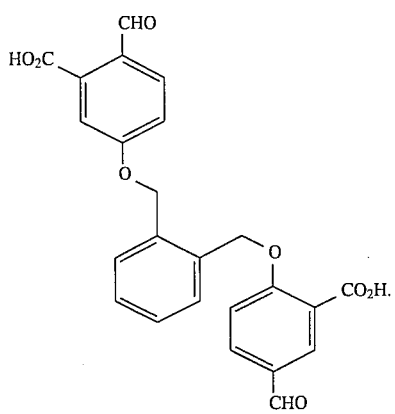

8. The compound of claim 1 wherein the chemical structure is:

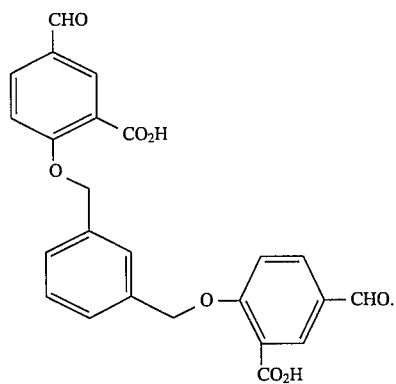

9. The compound of claim 1 wherein the chemical structure is:

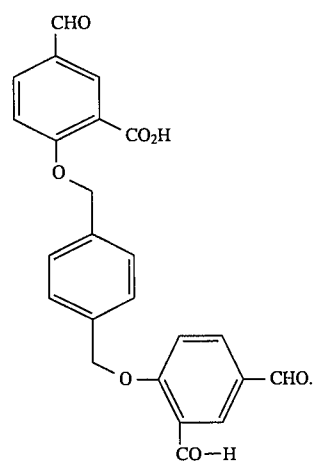

10. The compound of claim 1 wherein the chemical structure is:

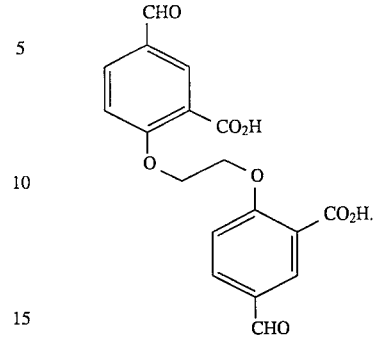

11. The compound of claim 1 wherein the chemical structure is:

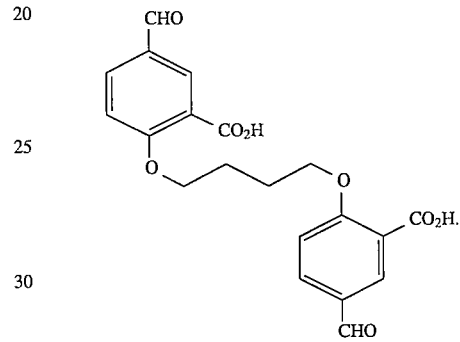

12. The compound of claim 1 wherein the chemical structure is:

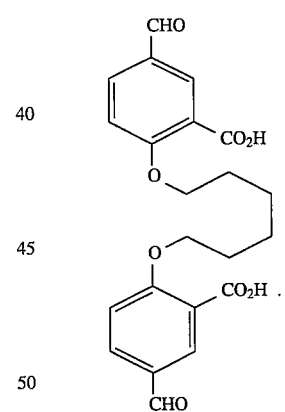

13. The compound of claim 1 wherein the chemical structure is:

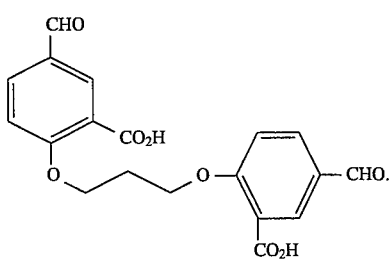

14. The compound of claim 1 wherein the chemical structure is:

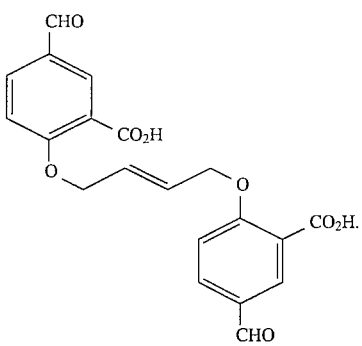

15. The compound of claim 1 wherein the chemical structure is:

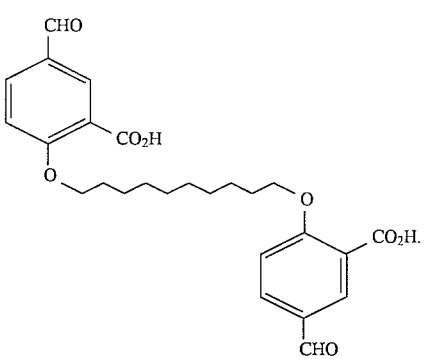

16. The compound of claim 1 wherein the chemical structure is:

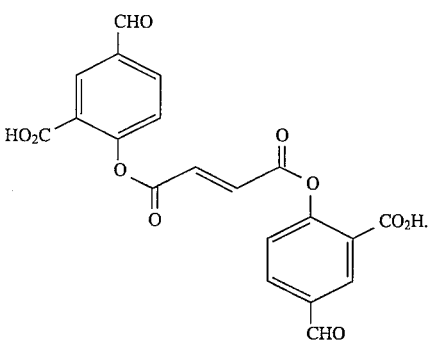

17. The compound of claim 1 wherein the chemical structure is:

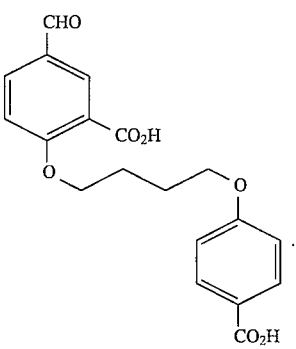

18. The compound of claim 1 wherein the chemical structure is:

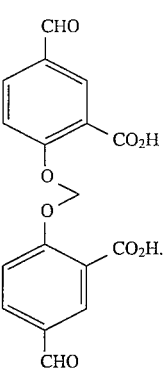

19. The compound of claim 1 wherein the chemical structure is:

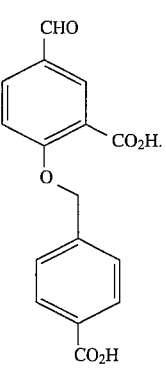

20. The compound of claim 1 wherein the chemical structure is:

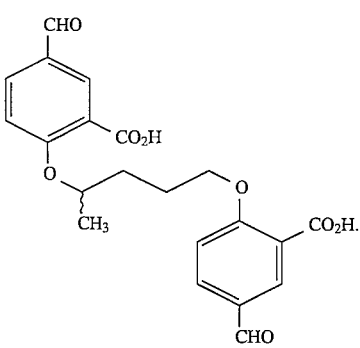

21. The compound of claim 1 wherein the chemical structure is:

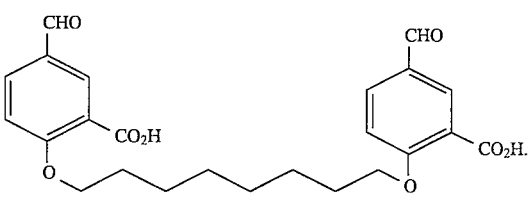

22. The compound of claim 1 wherein the chemical structure is:

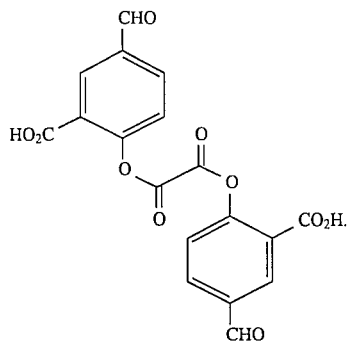

23. The compound of claim 1 wherein the chemical structure is:

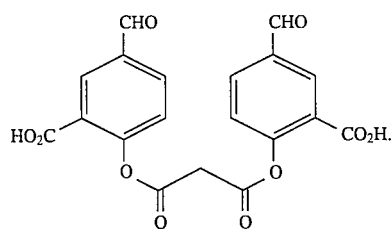

24. The compound of claim 1 wherein the chemical structure is:

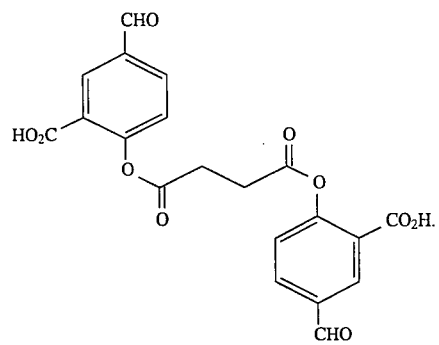

25. The compound of claim 1 wherein the chemical structure is:

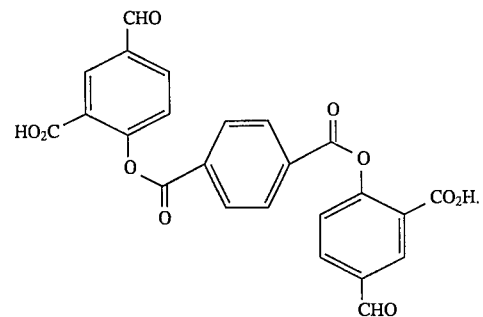

26. The compound of claim 1 wherein the chemical structure is:

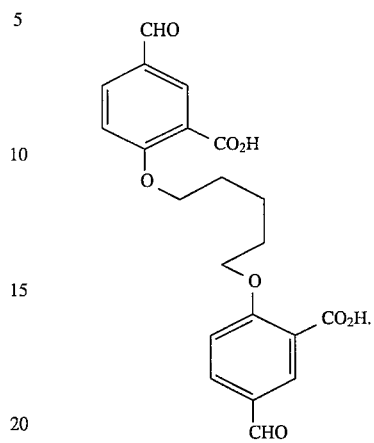

27. The compound of claim 3 wherein the chemical structure is:

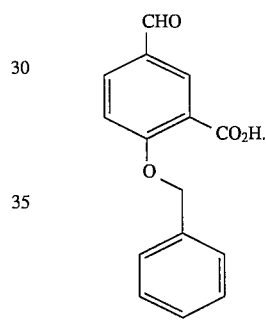

28. The compound of claim 3 wherein the chemical structure is:

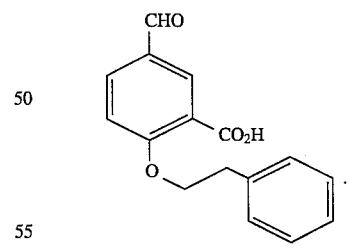

* * * * *